United States Patent [19]

Li et al.

[11] Patent Number: 5,534,631
[45] Date of Patent: Jul. 9, 1996

[54] CELLULAR FACTOR ILF

[75] Inventors: Ching Li, Hamden, Conn.; Richard B. Gaynor; Ajay Nirula, both of Dallas, Tex.

[73] Assignee: Board of Regents, The University of Texas System, Austin, Tex.

[21] Appl. No.: 906,930

[22] Filed: Jun. 30, 1992

[51] Int. Cl.$^6$ ............................ C12N 15/09; C07H 21/00
[52] U.S. Cl. .................... 536/23.1; 435/69.1; 435/240.2; 435/320.1; 435/254.11
[58] Field of Search ................................. 536/23.1, 24.1; 435/69.1, 240.1, 320.1, 240.2, 252.3, 254.11

[56] References Cited

PUBLICATIONS

Li, Ching et al., "Characterization and Chromosomal Mapping of the Gene Encoding the Cellular DNA Binding Protein ILF," *Genomics*, 13:665–671, 1992, published in USA.

Li, Ching et al., "Cloning of a Cellular Factor, Interleukin Binding Factor, That Binds to NFAT–like Motifs in the human Immunodeficiency Virus Long Terminal Repeat," *Proc. Natl. Acad. Sci. USA*, 88:7739–7743, 1991, published in USA.

Brunvand, Mark W. et al., "Nuclear Factors Interacting with the Mitogen–Responsive Regulatory Region of the Interleukin-2 Gene," *J. Biolog. Chem.*, 263(35):18904–18910, 1988, published in USA.

Lu, Yichen et al., "Identification of cis–Acting Repressive Sequences within the Negative Regulatory Element of Human Immunodeficiency Virus Type 1," *J. of Virol.*, 64(10):5226–5229, 1990, published in USA.

Mouzaki, Athanasia et al., "Silencing and Trans–Activation of the Mouse IL–2 Gene in Xenopus Oocytes by Proteins from Resting and Mitogen–Induced Primary T–Lymphocytes," *The EMBO Journal*, 10(6):1399–1406, 1991, published in Great Britain.

Lai, Eseng et al., "Hepatocyte Nuclear Factor 3α Belongs to a Gene Family in Mammals That Is Homologous to the Drosophila Homeotic Gene *fork head*," *Genes & Development*, 5:416–427, 1991, published in USA.

Flanagan, W. Michael et al., "Nuclear Association of a T–Cell Transcription Factor Blocked by FK–506 and Cyclosporin A," *Nature*, 352:803–807, 1991, published in Europe.

Tong–Starksen, Sandra E. et al., "Human Immunodeficiency Virus Long Terminal Repeat Responds to T–Cell Activation Signals," *Proc. Natl. Acad. Sci. USA*, 84:6845–6849, 1987, published in USA.

Siekevitz, Miriam et al., "Activation of the HIV–1 LTR by T Cell Mitogens and the Trans–Activator Protein of HTLV–I," *Science*, 238:1575–1578, 1987, published in USA.

Shaw, Jeng–Pyng et al., "Identification of a Putative Regulator of Early T Cell Activation Genes," *Science*, 241:202–205, 1988, published in USA.

Rosen, Craig A. et al., "The Location of Cis–Acting Regulatory Sequences in the Human T Cell Lymphotropic Virus Type III (HTLV–III/LAV) Long Terminal Repeat," *Cell*, 41:813–823, 1985, published in USA.

Klemsz, Michael J. et al., "The Macrophage and B Cell–Specific Transcription Factor PU.1 Is Related to the *ets* Oncogene," *Cell*, 61:113–124, 1990, published in USA.

Fujita, Takashi et al., "Regulation of Human Interleukin–2 Gene: Functional DNA Sequences in the 5' Flanking Region for the Gene Expression in Activated T Lymphocytes," *Cell*, 46:401–407, 1986, published in USA.

Gaynor, R. B. et al., "Repeated B Motifs in the Human Immunodeficiency Virus Type I Long Terminal Repeat Enhancer Region Do Not Exhibit Cooperative Factor Binding," *Proc. Natl. Acad. Sci. USA*, 85:9406–9410, 1988, published in USA.

Crabtree, Gerald R., "Contingent Genetic Regulatory Events in T Lymphocyte Activation," *Science*, 243:355–361, 1989, published in USA.

Wu, Foon et al., "tat Regulates Binding of the human Immunodeficiency Virus Trans–Activating Region RNA Loop–Binding Protein TRP–185," *Genes & Development*, 5:2128–2140, 1991, published in USA.

Gaynor, Richard, "Role of the Tar Element in Regulating HIV Gene Expression," *Advances in Molecular Biology and Targeted Treatment for AIDS*, A. Kumar, Ed., Plenum Press, New York, pp. 79–91, 1991, published in USA.

Wu, F. K. et al., "Purification of the Human Immunodeficiency Virus Type 1 Enhancer and TAR Binding Proteins EBP–1 and UBP–1," *The EMBO Journal*, 7(7):2117–2129, 1988, published in Europe.

(List continued on next page.)

*Primary Examiner*—Garnette D. Draper
*Assistant Examiner*—Sally P. Teng
*Attorney, Agent, or Firm*—Arnold White & Durkee

[57] ABSTRACT

A gene encoding a cellular factor that binds to NFAT-like elements in the HIV-LTR has been obtained by λgt11 expression cloning using oligonucleotides corresponding to these binding motifs. This cDNA encodes a ubiquitously expressed 60 kD protein, termed interleukin binding factor (ILF), which binds specifically to such purine rich motifs in the HIV-LTR. ILF also binds to similar purine-rich motifs in the IL-2 promoter, although with lower affinity than to HIV-LTR sequences. Sequence analysis reveals the ILF DNA binding domain to have strong homology with the recently described fork head DNA binding domain of the Drosophila homeotic protein, fork head, and a family of hepatocyte-nuclear factors, HNF-3. Other domains found in ILF include a nucleotide binding site, an N-glycosylation motif, a signal for ubiquitin-mediated degradation, and a potential nuclear localization signal. Results from cotransfection studies indicate that ILF is involved in positive and negative regulation of viral and cellular promoter elements. ILF activates IL-2 gene expression maxially when transfected at low concentrations, with a relative decrease in promoter activity being observed at high concentrations. ILF cDNA transfected into either unstimulated or stimulated T-cells inhibits gene expression under the transcriptional control of both IL-2 promoter and the HIV-1 LTR.

11 Claims, 33 Drawing Sheets

OTHER PUBLICATIONS

Weigel, Detlef et al., "The Homeotic Gene *fork head* Encodes a Nuclear Protein and Is Expressed in the Terminal Regions of the Drosophila Embryo," *Cell*, 57:645–658, 1989, published in USA.

Randak, Christoph et al., "Cyclosporin A Suppresses the Expression of the Interleukin 2 Gene by Inhibiting the Binding of Lymphocyte–Specific Factors to the IL–2 Enhancer," *The EMBO Journal*, 9(8):2529–2536, 1990, published in Europe.

Nabel, Gary and Baltimore, David, "An Inducible Transcription Factor Activates Expression of Human Immunodeficiency Virus in T Cells," *Nature*, 326:711–713, 1987, published in Europe.

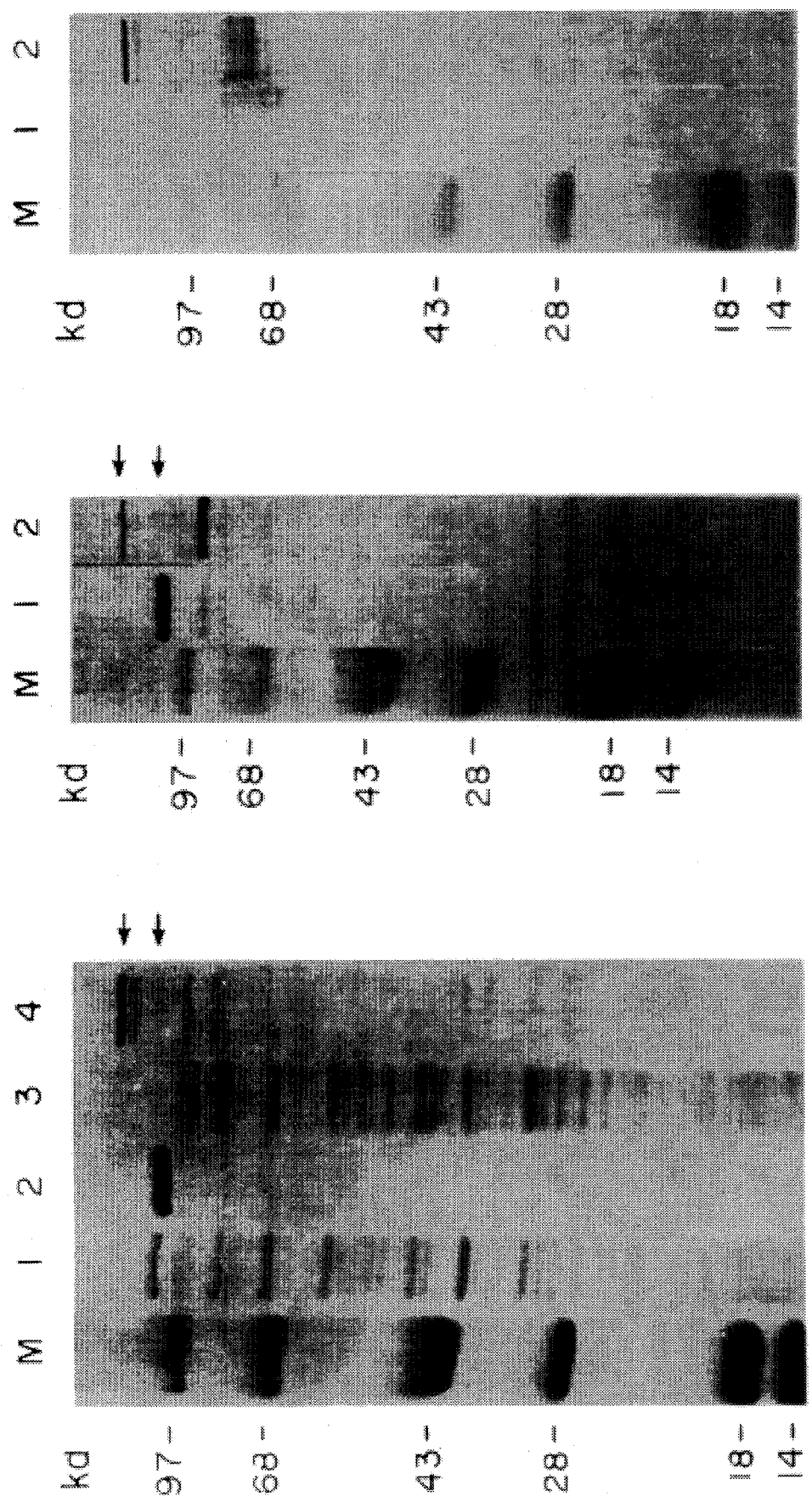

VFVDGVF QRRGAPPLQL PRVCTFRFPS TNIKITFTAL SSEKREKQEA SESPVKAVQP
HISPLTINIP DTMAHLISPL PSPTGTISAA NSCPSSPRGA GSSGYKVGRV MPSDLNLMAD
NSQPENEKEA SGGDSPKDDS KPPYSYAQLI VQAITMAPDK QLTLNGIYTH ITKNYPYYRT
ADKGWQNSIR HNLSLNRYFI KVPRSQEEPG KGSFWRIDPA SESKLIEQAF RKRRPRGVPC
FRTPLGPLSS RSAPASPNHA GVLSAHSSGA QTPESLSREG SPAPLEPEPG AAQPKLAVIQ
EARFAQSAPG SPLSSQPVLI TVQRQLPQAI KPVTYTVATP VTTSTSQPPV VQTVHVVHQI
PAVSVTSVAG LAPANTYTVS GQAVVTPAAV LAPPKAEAQE NGDHREVKVK VEPIPAIGHA
TLGTASRIIQ TAQTTPVQTV TIVQQAPLGQ HQLPIKTVTQ NGTHVASVPT AVHGQVNNAA
ASPLHMLATH ASASASLPTK RHNGDQPEQP ELKRIKTEDG EGIVIALSVD TPPAAVREKG
VQNZ

FIG. 3A

```
ILF      DSKPPYSYAQLIVQAITMAPDKQLTLNGIYTHITKNYPY
         •●XXXXXX    XX ●  XX •  XXX●•XX   X  • ●X
FKH      HAKPPYSYISLITMAIQNNPTRMLTLSEIYQFIMDLFPF
         XXXXXXXXXXXXXXXXXX •X••XXXXXXXXXX●XXXXXX •
HNF-3A   HAKPPYSYISLITMAIQQAPSKMLTLSEIYQWIMDLFPY

ILF      YRTADKGWQNSIRHNLSLNRYFIKVPRSQEEPGKGSFW
         XX  •●   XXXXXXXXXX●X X •X•XXX ●••XXXXXXX
FKH      YRQNQQRWQNSIRHSLSFNDCFVKIPRTPDKPGKGSFW
         XXXXXXXXXXXXXXXXXXX XXXX • X XXXXXXXXX● X
HNF-3A   YRQNQQRWQNSIRHSLSFNACFVKVARSPDKPGKGSYW

ILF      RIDPASESKLIEQAFRKRRPR
         •● X•X•●    •   • •X ●  X
FKH      TLHPDSGNMFENGCYLRRQKR
         XXXX XXXX●XXXXX XXXXXXX
HNF-3A   TLHPDSGNMFENGCYLRRQKR
```

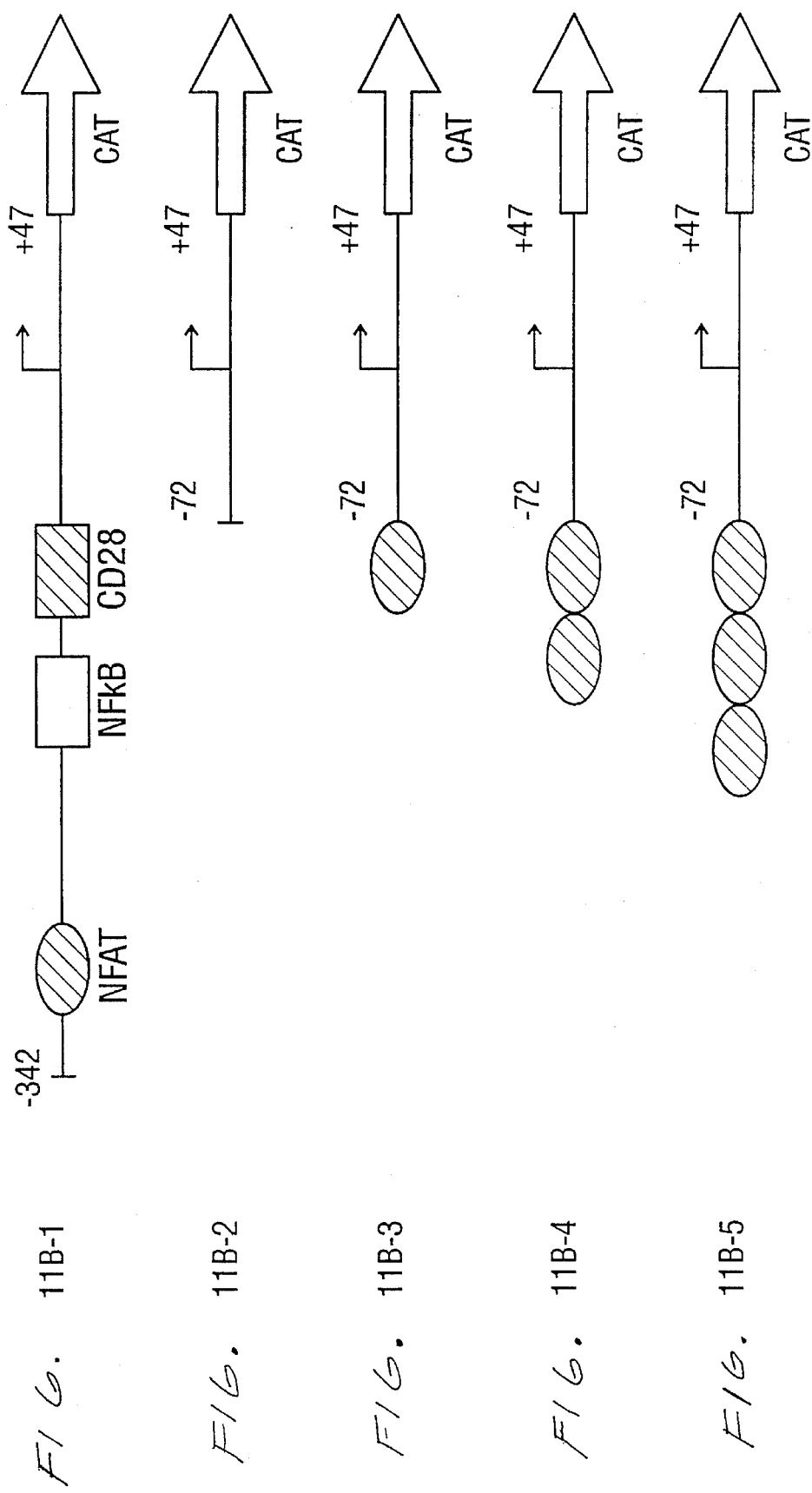

FIG. 14A

```
GTATTCGTGGACGGCGTGTTCCAGAGGCGGGGCCGCTGCAGCTGCCGCGCGTG      60
 V  F  V  D  G  V  F  Q  R  R  G  A  P  P  L  Q  L  P  R  V    20

TGCACATTCAGGTTCCCGAGCACAAACATCAAGATAACGTTCACTGCCCTGTCCAGCGAG  120
 C  T  F  R  F  P  S  T  N  I  K  I  T  F  T  A  L  S  S  E    40

AAGAGAGAGAAGCAGGAGGCCGTCTGAGTCTCCAGTGAAGGCCGTACAGCCACACATCTCG  180
 K  R  E  K  Q  E  A  S  E  S  P  V  K  A  V  Q  P  H  I  S    60

CCCCTGACCATCAACATTCCAGACACCATGGCCCACCTCATCAGCCCCTGCCCTCCCCCC  240
 P  L  T  I  N  I  P  D  T  M  A  H  L  I  S  P  L  P  S  P    80

ACGGGAACCATCAGCGCTGCAAACTCCTGCCCCTCCAGCCCCCGGGGAGAGGGGTCTTCA  300
 T  G  T  I  S  A  A  N  S  C  P  S  S  P  R  G  A  G  S  S   100

GGGTACAAGGTGGGCCGAGTGATGCCATCTGACCTCAATTTAATGGCTGACAACTCACAG  360
 G  Y  K  V  G  R  V  M  P  S  D  L  N  L  M  A  D  N  S  Q   120

CCTGAAAATGAAAAGGAAGCTTCAGGTGGAGACAGCCCGAAGGATGATTCAAAGCCGCCT  420
 P  E  N  E  K  E  A  S  G  G  D  S  P  K  D  D  S  K  P  P   140
```

FIG. 14B

```
TACTCCTACGCGCCAGCTGATAGTTCAGGGATTACGATGGCTCCGACAAACAGCTCACC    480
 Y  S  Y  A  Q  L  I  V  Q  A  I  T  M  A  P  D  K  Q  L  T     160

CTGAACGGGATTTATACACATCACTAAAAATTATCCCTACTACAGGACTGCGACAAG      540
 L  N  G  I  Y  T  H  I  T  K  N  Y  P  Y  Y  R  T  A  D  K    180

GGCTGGCAGAATTCAATTCCGCACAATCTCTCTGAATTCGTTATTTCATCAAAGTGCCG    600
 G  W  Q  N  S  I  R  H  N  L  S  L  N  R  Y  F  I  K  V  P    200

CGTTCCCAGGAAGAACCAGGCAAGGCTGTTCGGAGGATAGACCCAGCCTCTGAAAGC      660
 R  S  Q  E  E  P  G  K  G  S  F  W  R  I  D  P  A  S  E  S    220

AAATTAATAGAACAGGCTTTTAGGAAAACGACGGCTAGGGGTGCCCTGCTTTAGAACC     720
 K  L  I  E  Q  A  F  R  K  R  R  P  R  G  V  P  C  F  R  T    240

CCTCTGGGACCGCTCTCTTCTAGGAGTGCCTCCCAATCACGCGGGAGTGCTG           780
 P  L  G  P  L  S  S  R  S  A  P  A  S  P  N  H  A  G  V  L    260

CCCCAGACCCCAGAGAGCCTGTCGAGGAAGGTTCGCCGGCC                      840
 P  Q  T  P  E  S  L  S  R  E  G  S  P  A                      280

TCTGCTCACTCTAGTGGCCCAGACCCCAGAGAGCCTGTCGAGGAAGGTTCGCCGGCC
 S  A  H  S  S  G  A  Q  T  P  E  S  L  S  R  E  G  S  P  A
```

FIG. 14C

```
CCCCTGGAGCCTGAGCCTGGGCTGCACAGCCCAAACTCGCTGTCATCCAGGAAGCCCGG    900
 P  L  E  P  E  P  G  A  A  Q  P  K  L  A  V  I  Q  E  A  R    300

TTTGCCCAGAGCGCCCCAGGGTCACCTCTGTCCAGTCAGCCAGTCTTAATCACCGTCCAG    960
 F  A  Q  S  A  P  G  S  P  L  S  Q  P  V  L  I  T  V  Q       320

CGGCAGCTACCACAGGCCATCAAGCCTGTCACCTACACCGTGGCCACCCCAGTGACCACC   1020
 R  Q  L  P  Q  A  I  K  P  V  T  Y  T  V  A  T  P  V  T  T    340

TCGACCTCCCAGCCACCCGTCGTGCAGACCGTTCACGTCGTCCACCAGATCCCAGCGGTG   1080
 S  T  S  Q  P  P  V  V  Q  T  V  H  V  V  H  Q  I  P  A  V    360

TCGGTCACCAGTGTGGCCGGACTGGCCCCAGCGAACACGTACACTGTCTCTGGACAAGCT   1140
 S  V  T  S  V  A  G  L  A  P  A  N  T  Y  T  V  S  G  Q  A    380

GTGGTCACCCCGGCAGCCGTGCTGGCCCCTCCTAAGGCAGAGGCCCAGGAGAATGGAGAC   1200
 V  V  T  P  A  A  V  L  A  P  P  K  A  E  A  Q  E  N  G  D    400

CACAGGGAAGTCAAAGTGAAAGTAGAGCCTATTCCCGCCATTGGCCACGCGCTCGGC      1260
 H  R  E  V  K  V  K  V  E  P  I  P  A  I  G  H  A  T  L  G    420
```

FIG. 14D

```
ACTGCCAGCCGGATCATTCAGAGACGGGCACAGACCACCCCGGTCCAGACGGTGACCATAGTA    1320
 T  A  S  R  I  I  Q  T  A  Q  T  T  P  V  Q  T  V  T  I  V        440

CAACAGGCACCTCTAGGTCAACACCAGCTACCAATAAAAACTGTAACACAAAACGGCACT       1380
 Q  Q  A  P  L  G  Q  H  Q  L  P  I  K  T  V  T  Q  N  G  T        460

CACGTGGCATCAGTCCCCACTGCCGTCCACGGCCAGGTGAACAATGCCGGGGAGTCCT         1440
 H  V  A  S  V  P  T  A  V  H  G  Q  V  N  N  A  A  A  S  P        480

TTGCACATGTTGGCAACACACGCCATCCGGCCCTCCCTGCCCACAAAGCGCCACAAC          1500
 L  H  M  L  A  T  H  A  S  A  S  L  P  T  K  R  H  N             500

GGTGACCAGCCGGAGCAGCCGGAGCTGAAGCGGATCAAGACAGAAGACGGCGAGGCATC        1560
 G  D  Q  P  E  Q  P  E  L  K  R  I  K  T  E  D  G  E  G  I        520

GTCATTGCCCTGAGCGTGGACACGCCAGCCGCTAAGGGAAAAGGGTGTCCAGAAC            1620
 V  I  A  L  S  V  D  T  P  P  A  A  V  R  E  K  G  V  Q  N        540

TAGCGGACCGGGGAGAGCTTTTCTTTAACGATATCAACTTCTGTGGTGCCAAAAGGAGACGCG    1680

GCCTCCCCGCCAGCACTCGGGGGTGCAGGGCCCCTGTGGTTGGACTTCACCTCTCAGCACTG     1740
```

FIG. 14E

```
AAAACCCAAAACCCAGCTGGCCTTAACACTCCTTAAAGACAGAAGTCACACTTGAACAAA    1800
ACCCACACAACAAAACCTGATTTGGGAGACGGTGTCTCCACTGAGCACCTGCTGGGCT     1860
GAGCTTCTACCTACGAGTGAAACTCTGTCCTCCCGCGAGGACCAGGCATCGCTGTGTGAG   1920
GACGGCACGGCCAGCGCCTGCTGTGAGTGGGTCTCCCAAGACTAGGCCTCAGGACGCGGG   1980
GGGAGCCATCCCCGCCGCCCTCACAGACCCACCAGGCAGCGGAGACATGTGGAATTAGA    2040
GTATTTGAGGTGTCCTTTCTTTACAAAATAATGGGTCTTGGGCATTTCACATCACTCC     2100
ATTTCTACTGAGACTTTCAGAATCACACAGGCCCTTTCCGTGGATTTCATTTGGGCAAA    2160
GAAACAACATAGTTTTGTTTTTGTTTTCAGCCTATGGAATGATTTCCTTTTGTCTGTCTT   2220
GTTCAAGTTCAGACGAAGCTACTCTGGCATCTGCACATTTCCGTGTTACAGCAGCTGCCT   2280
GATGAATTTTATCCACCTCCATTTCAGCATGTGGCTCGCGTGGACAGGTGGACGGACGCT   2340
GTGGCCGCATGAACCTTGAGAACCCAGGGACGAGCCAGTGCCGGGAAGGAACTGCCGGG    2400
```

FIG. 14F

ACTCACCGAGCTGCACTTAACTGTTCTCTTTCTGGCTATTTTTTGTGTTGTTTCTTTG 2460

TGTTGACTTTGTCCCTGGCAAAATTTTCCACTCTGAGTAAAACAAGTCTCGGAATTC 2517

FIG. 15A

```
GTATTCGTGGACGGCGTGTTCCAGAGGCCGGGGCCGGCGAGCCTGCAGCTGCCGCGCGTG         60
 V  F  V  D  G  V  F  Q  R  R  G  A  P  P  L  Q  L  P  R  V         20

TGCACATTCAGGTTCCCGAGCACAAACATCAAGATAACGTTCACTGCCCTGTCCAGCGAG        120
 C  T  F  R  F  P  S  T  N  I  K  I  T  F  T  A  L  S  S  E         40

AAGAGAGAGAAGCAGGAGGCGTCTGAGTTCCAGTGAAGGCCGTACAGCCACACATCTCG        180
 K  R  E  K  Q  E  A  S  E  S  P  V  K  A  V  Q  P  H  I  S         60

CCCCTGACCATCAACATTCCAGACACCATGGCCCACCTCATCAGCCCTCTGCCCTCCCCC        240
 P  L  T  I  N  I  P  D  T  M  A  H  L  I  S  P  L  P  S  P         80

ACGGAACCATCAGCGCTGCAAACTGCCCATCTGACCTCAATTTAATGGCTGACAACTCACAG      300
 T  G  T  I  S  A  A  N  C  P  S  S  P  R  G  A  G  S  S         100

GGGTACAAGGTGGGCCGAGTGATGCCATCTGACCTCAATTTAATGGCTGACAACTCACAG       360
 G  Y  K  V  G  R  V  M  P  S  D  L  N  L  M  A  D  N  S  Q        120

CCTGAAAATGAAAAGGAAGCTTCAGGTGGAGACAGCCCGAAGGATGATTCAAAGCCGCCT      420
 P  E  N  E  K  E  A  S  G  G  D  S  P  K  D  D  S  K  P  P        140
```

FIG. 15B

```
TACTCCTACTAGGGCGCAGCTGATAGTAGTTCAGGGCGATTACGGATGGCTCCCGACAAACAGCTTACC   480
 Y  S  Y  A  Q  L  I  V  Q  A  I  T  M  A  P  D  K  Q  L  T            160

CTTGAAGGGATTTATACACATCACTAAAATTATCCCTACTACAGGACTGCGACAAG                540
 L  N  G  I  Y  T  H  H  T  K  N  Y  P  Y  Y  R  T  A  D  K            180

GGCTGGCACAATTCAATTCGCCACAATCTCTCTGAATCGTTATTTCATCAAGTGCCG                600
 G  W  H  N  S  I  R  H  N  L  S  L  N  R  Y  F  I  K  V  P            200

CGTTCCCAGGAAGAACCAGGCAAAGGCTGTTCTGGAGGATAGACCAGCCTTGAAAGC                660
 R  S  Q  E  E  P  G  K  G  S  F  W  R  I  D  P  A  S  E  S            220

AAATTAATAGAACAGGCTTTTAGGAAGACGGCTAGGGGGTGCCCTGCTTTAGAACC                  720
 K  L  I  E  Q  A  P  R  K  R  P  R  G  V  P  C  F  R  T               240

CCTCTGGGACGGCTCTCTTTCTAGGAGTGCCCCAGCCCTCCCAATCACGCGGGAGTGCTG              780
 P  L  G  P  L  S  S  R  S  A  P  A  S  P  N  H  A  G  V  L            260

TCTGCTCACTCTAGTGGCCCAGACCCCTGAGAGCCTGTCGAGGGAAGGTTCCGCCGGCC               840
 S  A  H  S  S  G  A  Q  T  P  E  S  L  S  R  E  G  S  P  A            280
```

FIG. 15C

```
CCCCTGGAGCCTGAGCCTGGGGCTGCACAGCCCAAACTCGCTGTCATCCAGGAAGCCCGG      900
 P   L   E   P   E   P   G   A   A   Q   P   K   L   A   V   I   Q   E   A   R       300

TTTGCCCAGAGCGCCCCAGGGGTCACCTCTCTGTCCAGTCAGCCAGTCTTAATCACCGTCCAG   960
 F   A   Q   S   A   P   G   S   P   L   S   S   Q   P   V   L   I   T   V   Q       320

CGGCAGCTACCACAGGCCATCAAGCCTGTCACCTACACTGTGGCCACCCCAGTGACCACC     1020
 R   Q   L   P   Q   A   I   K   P   V   T   Y   T   V   A   T   P   V   T   T       340

TCGACCTCCCAGCCACCCGTCGTGCAGACGGTTCACGTCGTCCACCAGATCCCAGCGGTG    1080
 S   T   S   Q   P   P   V   V   Q   T   V   H   V   V   H   Q   I   P   A   V       360

TCGGTCACCAGTGTGGCCGGACTGGCCCCAGCGAACACGTACACTGTCTCTGGACAAGCT    1140
 S   V   T   S   V   A   G   L   A   P   A   N   T   Y   T   V   S   G   Q   A       380

GTGGTCACCCCGGCCGCAGCCGTGCTGGCCCCTCCTAAGGCAGAGGCCCAGGAGAATGGAGAC 1200
 V   V   T   P   A   A   V   L   A   P   P   K   A   E   A   Q   E   N   G   D       400

CACAGGGAAGTCAAAGTAGAGCCTATTCCCGCCATTGGCCACGCTCGGC              1260
 H   R   E   V   K   V   K   V   E   P   I   P   A   I   G   H   A   T   L   G       420
```

FIG. 15D

```
ACTGCCAGCCGGATCATTCAGACGGCACAGACCACCCGGTCCAGACGGTGACCATAGTA  1320
 T  A  S  R  I  I  Q  T  A  Q  T  T  P  V  Q  T  V  T  I  V   440

CAACAGGCACCTCTAGGTCAACACCAGCTACCAATAAAAACTGTAACACAAAACGGCACT  1380
 Q  Q  A  P  L  G  Q  H  Q  L  P  I  K  T  V  T  Q  N  G  T   460

CACGTGGCATCAGTCCCCACTGCGGTTCCAAGGCCCAGGTGAACAATGGGCCCCTTGGCCTC  1440
 H  V  A  S  V  P  T  A  V  H  G  Q  V  N  N  G  P  L  G  L   480

AGAAGGCCCCATGTGCCAGCTCAGTTGAGTTGCTTCAGTTGACACAGCAGGCCCAT  1500
 R  R  P  C  A  S  D  W  S  C  L  S                          494

CCAGAACAGACCAGCAGGTGCTTCTGGAGACAAGAGCAAAGCCTTTTCCGGCAGCCGGGAA  1560

GCTGGGATGAGAAACGAGCAGGTTGTCCAGAAGGTTGTCCAGAGACACTTGTCGATGCTGT  1620

TCCGGAGTCAGCGGTAGGAGGAGAAGGCCACTGGCGAAACCAGAGTCACACTGCCGCTCTGTGCCAT  1680

CTCTGCCTACCGCCCAGTGCCGCTGTCTCTGCACATTTTTGTAGACATTAGAGTCG  1740

GTTGAGGGCCACCTGCGGGCGGCCACCGCCACAGACTGGCGGCGGATTGCAGGGAG  1800
```

FIG. 15E

```
GAGCATCTGAGGTGGTCACGGGTGTGCCCAGTCACACCAACTGCAGCCGGGGGGAGTC    1860
CTTTGCACATGTTGGCAACACAGCGATCCGCCCTGCCCACAAAGCGCCACA            1920
ACGGTGACCAGCCCGGAGCAGCCGGAGCTGAAGCGGATCAAGACAGAAGACGGCGAGGGCA 1980
TCGTCATTGCCCTGAGCGGTGACACGCCACCGGCCAGCCGTAAGGAAAAGGGTGTCCAGA  2040
ACTAGCGACCCGGGAGAGCTTTTCTTTAACGATATCAACTCTGTGGTGCCAAAAGGAGACG 2100
CGGCCCTCCCCGCCAGCACTCGGGGGTGCAGGGCCCTGTGGTTGGACTTCACCTCTCAGCAC 2160
TGAAAAACCCAAAACCCAGCTGGCCCTTAAACACTCCTTAAAGACAGAAGTCACACTTGAACA 2220
AAACCCACACAACAAAACCTGATTTGGGAGACGGTGTCTCCACTGAGCACCTGCTGGG     2260
CTGAGCTTCTACCTACGAGTGAAACTCTGTCCTCCCGGAGGACCAGGCATCGCTGTGTG   2320
AGGACGGCCAGGCCAGCGCTGCTGTGAGTGGGTCTCCCAAGACTAGGCCTCAGGACGCG   2380
GGGGAGCCATCCCCGCCCTCACAGGACCCACCAGGCGCCAGCGGAGACATGTGGAATTA   2440
```

FIG. 15F

```
GAGTATTTGAGGTGTCCTTTCTTTACAAAATAATGGGGTCTTGGGCATTTCACATCACT  2500
CCATTTCTACTGAGACTTTCAGAATCACACAGGCCCTTTCCGTGGATTTCATTGGGGCA  2560
AAGAAACAACATAGTTTTGTTTTCAGCCTATGGAATGATTCCTTTGTCTGTC        2620
TTGTTCAAGTTCAGACGAAGCTACTCTGGCATCTGCACATTCCGTGTTACAGCAGCTGC  2680
CTGATGAATTTATCCACCTCCATTTCAGCATGTGGCTCGCGTGGACAGGTGGACGGACG  2740
CTGTGGCCGCATGGAACCTTGAGAACCCAGGACGAGCCAGTGCCGGGAAGGAACTGCCG  2800
GGACTCACCGAGCTGCACTTAACTGTTCTCTTTCTGGCTATTTTTTGTTGTTTCTT     2860
TGTGTTGACTTTGTCCCTGGCAAAATTTCCACTCTGAGTAAAACAAGTCTCGGAATTC   2919
```

CELLULAR FACTOR ILF

BACKGROUND OF THE INVENTION

1. Field of the Invention

The present invention relates generally to the field of cellular factors (proteins) which bind nucleic acids, particularly those factors which bind the nucleic acid region previously found to bind a factor or group of factors known as the nuclear factor of activated T cells (the NFAT region). The gene which encodes the cellular factor is also related to the field of the present invention. Recombinant vectors and host cells including the gene for the cellular nucleic acid binding factor is also related to the present disclosure. The invention also relates to the field of methods for regulating the expression of cellular and viral genes including lymphokine genes such as IL-2 and HIV gene expression, and to methods for treating HIV and AIDS infection.

2. Description of the Related Art

The human immunodeficiency virus (HIV) is the causative agent of AIDS. In common with other retroviruses, HIV contains two long terminal repeats (LTRs) and three conserved genes, namely gag, pol, and env. Once HIV-1 integrates into the host cell genome, its gene expression is regulated by cellular transcription factors in a manner similar to that of endogenous cellular genes. The activities of several of the cellular transcription factors which bind to the HIV-1 LTR are altered by parameters such as activation or differentiation of lymphocytes or macrophages, the action of lymphokines, and alterations of signal transduction pathways. Thus, HIV is subject to many of the same regulatory signals that are important in controlling cellular gene expression.

A number of elements in the HIV long terminal repeat (LTR), including SP1, TATA, and TAR are involved in regulating gene expression in a variety of cell lines (Garcia et al., 1989). At least two other regulatory regions have been determined to be important for activation of HIV-LTR gene expression in activated T-lymphocytes. One is the enhancer region extending from nucleotides −103 to −78 which contains two NF-kappa B motifs (Nabel & Baltimore, 1987; Tong-Starksen et al., 1987; Gaynor et al., 1988). The other is a region extending from nucleotides −283 to −195 which contains several motifs with homology to a critical regulatory domain in the interleukin-2 (IL-2) promoter (Fujita et al., 1986; Shaw et al., 1988; Crabtree, 1989).

The referenced regulatory domain of the IL-2 promoter is characterized as a motif which is a positive acting element. This positive acting element binds a cellular factor known as the nuclear factor of activated T-cells (NFAT) whose binding is strongly induced in activated T-cells (Fujita et al., 1986; Shaw et al., 1988; Crabtree, 1989). NFAT is composed of two subunits, a constitutive nuclear factor and an inducible T-cell factor. In the HIV-LTR, this region containing NFAT-like motifs is important for increasing HIV gene expression in activated T-cells (Siekevitz et al., 1987), but also appears to have negative regulatory effects on HIV gene expression in the presence of tat (Siekevitz et al., 1987; Lu et al., 1990).

Certain poorly characterized cellular proteins have been reported to bind to NFAT-like regulatory motifs. In activated T-cells, UV crosslinking studies are said to demonstrate that three cellular proteins of 90 kD, 45 kD, and 25 kD bind to the NFAT motif in the IL-2 promoter (Randak et al., 1990). Cyclosporin inhibits the binding of each of these proteins, suggesting that multiple proteins with a similar pattern of regulation may bind to this region. Recently, a cellular factor restricted to B lymphocytes and macrophages, known as PU.1 (Pettersson & Schaffner, 1987; Klemsz et al., 1990), which has strong homology to the ets proto-oncogene, was found to bind to a related motif found in SV 40 (Karim et al., 1990). Thus, different DNA binding proteins may be capable of binding to these purine-rich motifs.

A macrophage and B-cell-specific transcription factor, PU.1, with homology to the ets oncogene, also binds to a purine-rich sequence GAGGAA identical to that found in the NFAT motif (Klemsz et al., 1990). This protein has been demonstrated to have positive effects on SV40 gene expression (Karim et al., 1990).

Despite the studies discussed above, there remains relatively little documented information on cellular factors which are capable of binding to the NFAT-like motifs in the HIV-LTR. In particular, the mechanisms by which this region can exert both positive and negative regulation on HIV gene expression remain to be elucidated.

Disturbances of T cell regulation have been implicated in immune system pathology such as immunodeficiency and autoimmune disorders, and may also play an important role in the development of AIDS following latent HIV infection. The identification of NFAT regulatory factors would represent an important advance in the knowledge of IL-2 and HIV gene regulation, and would thus further the understanding of the processes underlying immune homeostasis, disease, and AIDS. Such a discovery may also open up new avenues of clinical investigation, including the development of AIDS- and immune-therapeutic agents.

The nucleotide sequence of the HIV-LTR reveals several purine-rich motifs between nucleotides −283 and −195 having a homology to an element in the IL-2 promoter (Fujita et al., 1986). This element is a binding site for the cellular factor, NFAT, whose binding is induced in activated T-cells (Fujita et al., 1986; Shaw et al., 1988; Crabtree, 1989). Indeed, in addition to regulation by general transcription factors, HIV gene expression is likely regulated by NFAT (Crabtree, 1989). In the HIV LTR, the −283 to −195 region containing the NFAT-like motifs is important for increasing HIV gene expression in activated T-cells but it has little effect on basal gene expression (Siekevitz et al., 1987). However, in the presence of tat it appears to have negative regulatory effects on HIV gene expression (Rosen et al., 1985).

DNase I footprinting demonstrates the binding of cellular factors from −254 to −216 in the HIV-LTR with extracts prepared from activated but not resting T-cells (Shaw et al., 1988; Crabtree, 1989). An increase in NFAT binding precedes the activation of both IL-2 and HIV gene expression in stimulated T-cells (Shaw et al., 1988; Crabtree, 1989). The induction of NFAT binding requires new protein synthesis (Shaw et al., 1988; Crabtree, 1989), and its binding is inhibited by cyclosporin, an inhibitor of the enzyme cyclophilin (Emmel et al., 1989). However, the production of NFAT is not completely restricted to activated T-cells since low levels of NFAT binding are also detected in resting T-cells (Novak et al., 1990).

Multiple cellular proteins have also been demonstrated to bind to the NFAT-motifs in the IL-2 promoter (Randak et al., 1990). As already noted, the binding of NFAT is strongly induced by T-cell activation.

It appeared to the present inventors that specific proteins which bind to the NFAT-like motif were important in regulating HIV gene expression. The inventors therefore proceeded to examine the various characteristics which such an NFAT—binding factor would have in their attempt to isolate and characterize a specific and unique binding factor. Such a protein/factor which was capable of binding an NFAT-motif on the HIV or which would bind the protein which binds the NFAT motif region of the HIV-LTR, would provide a specific and unique method for inhibiting HIV-1 gene expression, and thereby the method for inhibiting the pathologies in humans which HIV-1 infection causes, such as AIDS and ARC.

DNA sequences set forth in Table 1 including the Interleukin-2 gene (see Table 1, supra). These sequences include the following:

| | | | | | | | | | | | | | | |
|---|---|---|---|---|---|---|---|---|---|---|---|---|---|---|
| IL-2: SEQ ID NO: 7 | -291 | A | G | A | A | G | G | A | G | G | A | A | A | A | -277 |
| HIV distal: SEQ ID NO: 8 | -276 | C | C | A | A | T | G | A | A | G | G | A | G | A | G | A | -260 |
| HIV prox: SEQ ID NO: 9 | -221 | G | A | C | G | C | G | G | A | G | A | A | A | G | A | A | -260 |
| MHC: SEQ ID NO: 10 | -70 | C | C | A | A | G | T | G | A | G | G | A | A | C | C | A | -56 |
| SV40 PU box: SEQ ID NO: 11 | -319 | C | T | G | A | A | A | G | A | G | G | A | A | C | T | T | -305 |

SUMMARY OF THE INVENTION

The present invention discloses a unique nucleic acid binding factor. This factor is designated interleukin binding factor (ILF) by the present inventors. The nucleic acid binding factor has been identified by the present inventors as having a unique combination of characteristic features. Specifically, the nucleic acid binding factor of the present invention has been characterized as having the ability to bind to an NFAT-like nucleic acid binding site on the HIV-LTR and as being capable of both activating and inhibiting HIV gene expression.

The inventors have isolated one form of ILF binding factor protein which has a molecular weight of 60 kDa. However, due to alternative splicing of mRNA present in the cell, alternative forms of the ILF protein can be produced resulting in proteins of either lower or higher molecular weight. Furthermore, the apparent molecular weight of proteins, as determined experimentally, is known to be variable. For example, it is known that the migration of a polypeptide can vary, sometimes significantly, under different conditions of SDS/PAGE (Capaldi et al., 1977). It will therefore be appreciated that under differing electrophoretic conditions, for example, the apparent molecular weights of the proteins of the present invention may vary from that quoted above.

Examples of the amino acid sequence of the nucleic acid binding factor protein of the invention are provided in SEQUENCE ID NO: +2 and SEQUENCE ID NO: 33. Proteins with such amino acid sequences or their biological equivalents constitute one embodiment of the claimed invention.

The factor is known also to contain a fork head DNA binding domain. The acronym, "NFAT", stands for Nuclear Factor of Activated T-cells. As will be recalled, nuclear factor of activated T-cells is one of several cellular factors which is involved in IL-2 gene expression.

The present inventors have found that the nucleic acid binding factor, ILF, is capable of binding to a purine rich region in the HIV-LTR promoter between −283 and −195, and is capable of both activating and inhibiting HIV gene expression depending on the concentration of the factor in the cells. Hence, the nucleic acid binding factor of the present invention may be employed in regulating HIV gene expression, and may have utility in inhibiting HIV gene expression in vivo. For example, the ILF will be useful in the treatment of such HIV-related disorders as AIDS and ARC.

The nucleic acid factor of the present invention may be further defined as having the ability to bind to the NFAT-like nucleic acid binding factor may further be defined as capable of regulating gene expression of both viral and cellular proteins. The nucleic acid binding factor of the invention has been characterized as a protein comprising about 11% proline, about 10% serine and about 8% threonineo In another aspect of the present invention, a DNA segment encoding a nucleic acid binding protein as set forth above is provided. Most specifically, the DNA segment is defined as a cDNA. The DNA segment may be further defined as including a nucleic acid sequence essentially as set forth herein in SEQUENCE ID NO: 1 or SEQUENCE ID NO: 3. The referenced DNA segment may be further defined as encoding a binding protein which includes an amino acid sequence essentially as set forth in SEQUENCE ID NO: +2 or SEQUENCE ID NO: 33, which are also provided in FIGS. 14 and 15, respectively.

In still another aspect of the invention, a recombinant vector comprising a DNA segment as described above is provided. The protein encoded by the DNA segment is capable of regulating the expression of an interleukin-2 gene in T-lymphocytes. The present invention also comprises a recombinant host cell which incorporates a recombinant DNA segment corresponding to the DNA segments of those encoding DNA segments for the nucleic acid binding factor ILF described herein. The recombinant host cell may be further defined as including a recombinant vector sequence. By way of example, the recombinant vector sequence is pDp 18.

Most preferably, the recombinant host cell is a eukaryotic host cell. However, it is anticipated that prokaryotic host cells may be equally efficacious in the practice of the present invention. The recombinant host cell may be defined as a bacterial host cell. Within the herein described recombinant host cell, the DNA segment may be further defined as integrated into the genome of the host cell. Most preferably, this DNA segment is positioned on a recombinant vector. By way of example, such a recombinant vector is known as pGEX in which a portion of the glutathione-S-transferase gene is located upstream of the inserted gene so that a fusion protein can be generated. (Smith, D. B. and Johnson, K. S. (1988) single-step purification of polypeptides expressed in *Escherichia coli* as fusions with glutathione-S-transferase 67:31–40.) This vector is sold by Pharmacia.

In still anther aspect of the present invention, a nucleic acid segment which comprises at least a ten nucleotide long (length) stretch which corresponds to the nucleic acid sequence shown in SEQUENCE ID NO: 1 (see FIG. 14) or SEQUENCE ID NO: 3 (see FIG. 15) is provided. The nucleic acid segment of the present invention may comprise a nucleic acid fragment having up to 200 base pairs. A more preferred embodiment of the described nucleic acid segment comprises about 100 nucleotides, or more preferred, at least 50 nucleotides which corresponds again to the nucleic acid sequence provided herein at SEQUENCE ID NO: 1 or SEQUENCE ID NO: 3.

An even more preferred embodiment of the herein described nucleic acid segment comprises at least 30 nucleotides which correspond to the nucleic acid sequence of SEQUENCE ID NO: 1. In a most preferred embodiment, the nucleic acid segment comprises at least 20 nucleotides corresponding again to the nucleic acid sequence provided at SEQUENCE ID NO: 1. A more preferred embodiment may be further defined as comprising at least a 15 nucleotide long stretch corresponding to the referenced SEQUENCE ID NO: 1.

Another aspect of the present invention provides a method for modulating the expression of a cellular or a viral gene. Most preferably, this method comprises introducing a nucleic acid binding factor into a cell containing a gene including NFAT-like DNA sequences. The nucleic acid binding factor is more particularly defined as capable of binding to an NFAT-like nucleic acid binding motif of HIV-LTR, of activating and inhibiting HIV gene expression and containing a fork head DNA binding domain.

The nucleic acid binding element ILF of the present invention may be further described as either enhancing (stimulating) or inhibiting HIV gene expression depending upon the concentration of the binding factor used.

The method for modulating the expression of a cellular or viral gene of the present invention may be further defined as employing a DNA binding factor which is introduced into the cell at a level or concentration sufficient to stimulate the expression of a cellular or viral gene. Activation of HIV-1 gene expression is seen at about 1 µg of ILF and inhibition is seen at about 10 µg of ILF. The studies to determine the concentration of ILF which inhibits or activates HIV-1 gene expression involves electroporation of Jurkat cells ($5\times10^6$ to $10^7$ cells) with an HIV LTR CAT plasmid (1 µg) in both the presence and absence of the tat gene (1 µg). ILF expression vectors (between 0.5 µg to 10 µg) were also transfected.

By way of example, it is contemplated that expression, either enhanced or decrased, of a cellular gene may be achieved by introducing the nucleic acid binding factor into a cell at a concentration ranging from $10^{-8}$ to $10^{-12}$M. Most cellular transcription factors are present in a concentration range from 10,000 to 200,000 molecules/cells.

The described method may also be employed to repress or inhibit the expression of a cellular or viral gene. For such an application, the DNA binding protein may be introduced into the cell at a level or concentration of about 10 µg ILF DNA/$10^7$ cells. The optimal concentrations to be used are expected to be different, particularly depending on if it is a cellular or a viral gene to be inhibited.

Where the method is employed to repress or inhibit gene expression, the gene may be either viral or cellular. Where the gene is viral, the viral gene for which repression or inhibition will be provided according to the claimed method is an HIV gene. In contrast, where the method is employed to enhance or stimulate gene expression, the gene is most preferably a cellular gene. By way of example, such a cellular gene may be the interleukin-2 gene. It may be useful to either activate or repress the expression of the interleukin-2 gene depending on the clinical utility desired.

The uses of ILF would include the inhibition of HIV-1 gene expression. Introduction of peptides which antagonize the binding of ILF to the HIV LTR is one mechanism proposed by the inventors to inhibit ILF activity. Those peptides which correspond to portions of the ILF fork head binding domain will be added to HIV infected cells over a wide concentration range from $10^{-6}$M to $10^{-12}$M. Most preferably, the concentration range of the DNA binding actor to be used+is between a level of about $10^{-9}$M to $1-^{-12}$M. In this manner, inhibition of HIV-1 gene expression by ILF peptide analogues can be achieved.

Since ILF also binds to sequences in the IL-2 gene, ILF peptide analogues may also be used to inhibit IL-2 gene expression. Peptides ($10^{-6}$M to $10^{-12}$M) corresponding to the ILF fork head DNA binding domains will be added to either unstimulated or PHA and PMA stimulated Jurkat cells. The level of IL-2 secreted into the tissue culture media will be measured. The relative potency of these peptides in the inhibition of IL-2 gene expression can thus be more narrowly defined.

These peptides may also be studied in animal models such as mouse models with autoimmune diseases whose clinical course is worsened by activated T-cells. Likewise, the SCID-hu mouse model which can support the growth of HIV-1 infected human cells will also be tested with these peptides. Results with the mouse models will therefore indicate at what concentration these peptides inhibit IL-2 or HIV-1 gene expression in vivo, and therefore the even further efficacy of the peptide for human HIV-1 infection or autoimmune diseases.

Immunosuppressive agents such as cyclosporin and FK 506 are believed to inhibit the function of the NFAT protein complex. The mechanism by which these compounds may inhibit NFAT, however, is not known. The inventors postulate that ILF is a protein in the NFAT complex. If so, immunosuppressive agents which inhibit NFAT and thus IL-2 gene expression may also inhibit the ability of ILF to interact with other proteins in the NFAT complex. Novel inhibitors related to cyclosporin and FK 506 which more specifically interfere with ILF interactions with proteins in the NFAT complex may therefore be useful in inhibiting either HIV or IL-2 gene expression.

ILF is located on chromosome 17q25. This region is a site of deletions in human leukemia and potentially other human malignancies. Thus the loss of ILF function may be involved in the generation of human leukemia or other human malignancies. The use of the ILF cDNA (such as the cDNA defined in SEQUENCE ID NO: 1 and SEQUENCE ID NO: 3) cloned into retroviral expression vectors may thus be used to inhibit leukemic or other malignant cells. Samples from a variety of leukemia patients in particular and patients suffering from other malignancies will be screened with the ILF cDNA disclosed herein by Northern and Southern analysis and PCR. Cells which contain alterations in the ILF gene will be further characterized. Populations of such cells will be infected with retrovirus vectors containing ILF and screened for the neomycin drug resistance gene with the compound G418, contained in these vectors. The leukemia cells containing ILF introduced by retroviral vectors will be studied for their growth properties as compared to cells lacking ILF. Thus, ILF may be a factor that can inhibit some human leukemias. Retroviral vectors will also be used to infect leukemia cells lacking the ILF gene. In addition ILF will be introduced into cells using other methods, including liposomes, for potential human therapy.

It is contemplated from the results provided herein that the described binding factor, ILF, may also be employed in a method for treating an HIV or an AIDS infection in an animal. In one embodiment, such a method would comprise identifying an animal having an HIV or an AIDS infection and treating the animal with a therapeutically effective amount of the nucleic acid binding factor described herein or a vector including a nucleic acid segment as described. The amount to be administered in either case should be provided in a concentration or amount sufficient to inhibit HIV or AIDS virus expression. The nucleic acid binding element is more specifically described as interleukin binding factor as characterized by the present inventors.

According to the claimed method, an HIV or an AIDS infection in an animal may be identified by a positive serological test for an HIV or AIDS viral antigen or an anti-HIV or anti-AIDS antibody. However, either methods known to those of skill in the art of HIV and AIDS diagnosis may be used with equal efficacy in conjunction with the present invention to identify an animal or patient with an HIV or AIDS infection. The presently described methods may therefore be efficaciously used in the treatment of HIV or AIDS infection in humans.

The following abbreviation are used throughout the description of the present invention.

NFAT=nuclear factor of activated T cells
ILF=interleukin binding factor
LTR=long terminal repeat
HIV=human immunodeficiency virus
PDP=a eukaryotic expression plasmid
CAT=chloramphenicol acetyltransferase
PCR=polymerase chain reaction
SEQ ID NO: 1=ILF-1 cDNA sequence
SEQ ID NO: 2=ILF-1 protein sequence
SEQ ID NO: 3=ILF-2 cDNA sequence
SEQ ID NO: 33=ILF-2 protein sequences

BRIEF DESCRIPTION OF THE DRAWINGS

FIG. 14. The nucleotide sequence of ILF-1 cDNA and the amino acid sequence of ILF-1. The 3043 bp nucleotide sequence of a partial ILF-1 cDNA and the portion containing a 543-amino acid open reading frame is shown. The portion of the open reading frame containing homology with the fork head DNA-binding domain is shaded. SEQUENCE ID NO: 1 (cDNA for ILF-1) and SEQ ID NO: 2 (amino acid sequence for ILF-1) are shown.

FIG. 15. Nucleotide sequence of the ILF-2 cDNA and the amino acid sequence of ILF-2. The 3465-bp nucleotide sequence of a partial ILF-2 cDNA and the portion containing a 497-amino acid open reading frame is shown. The portions of the open reading frame containing the homology with the fork head DNA binding domain and that region differing from the ILF-1 are shaded. SEQUENCE ID NO: 3 (cDNA for ILF-2) and SEQ ID NO: 33 (amino acid sequence for ILF-2) are shown.

DETAILED DESCRIPTION OF THE PREFERRED EMBODIMENTS

Figure 2:
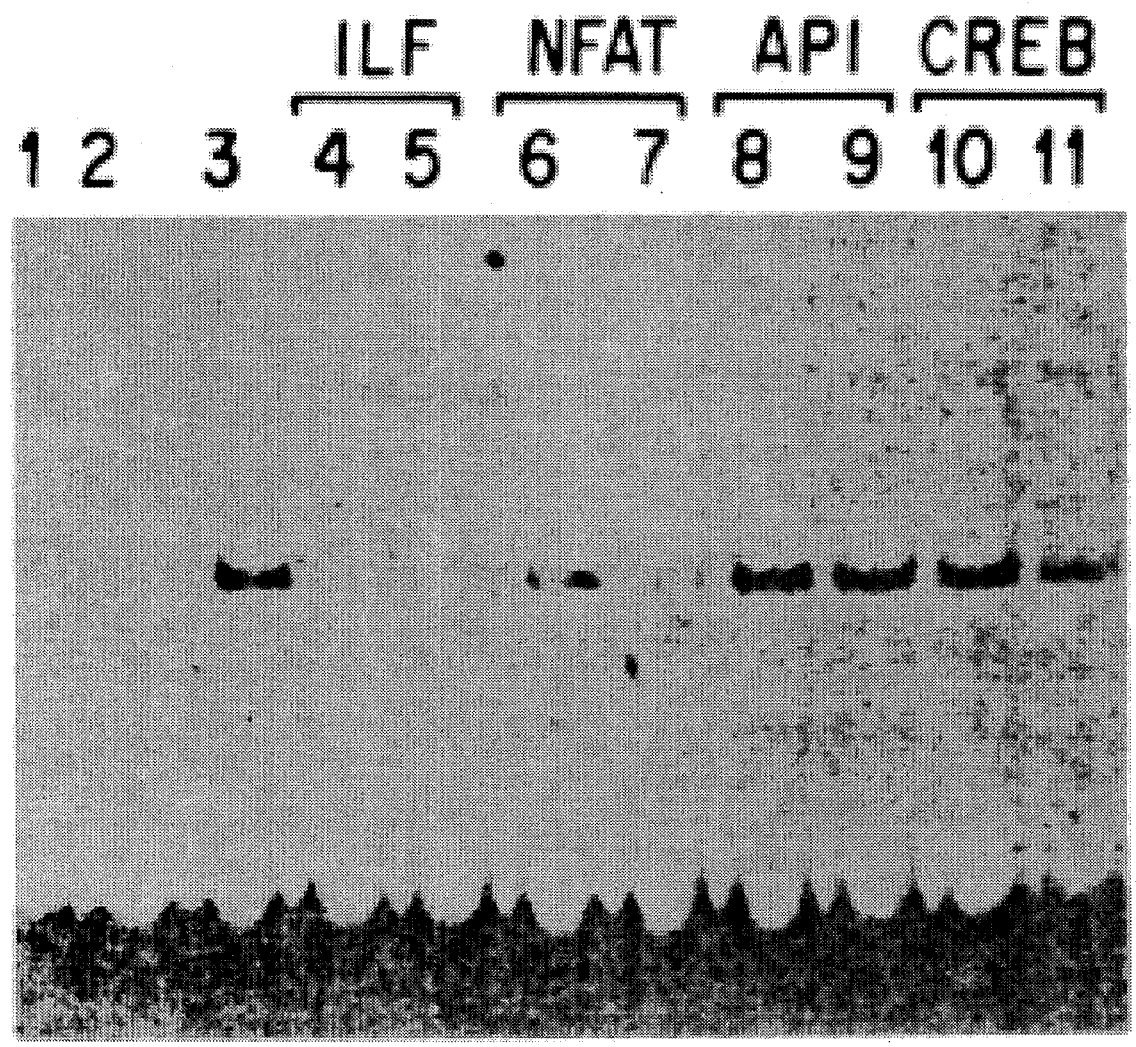
FIG. 2. Gel retardation analysis with β-galactosidase/ILF fusion protein. An HIV-LTR fragment extending from −310 to −255 was used in gel retardations with either β-galactosidase or β-galactosidase/ILF purified with anti-β-galactosidase sepharose chromatography. Lane 1, probe alone; lane 2, probe with 3 μg of β-galactosidase extract; lane 3, probe with 3 μg of β-galactosidase/ILF extract. Competition analysis with either a 10-fold (lanes 4, 6, 8, 10) or 50-fold (lanes 5, 7, 9, 11) molar excess of unlabeled oligonucleotides corresponding to ILF (lanes 4 and 5), NFAT (lanes 6 and 7), AP1 (lanes 8 and 9) and CREB (lanes 10 and 11) binding motifs are shown.
Figure 3B:
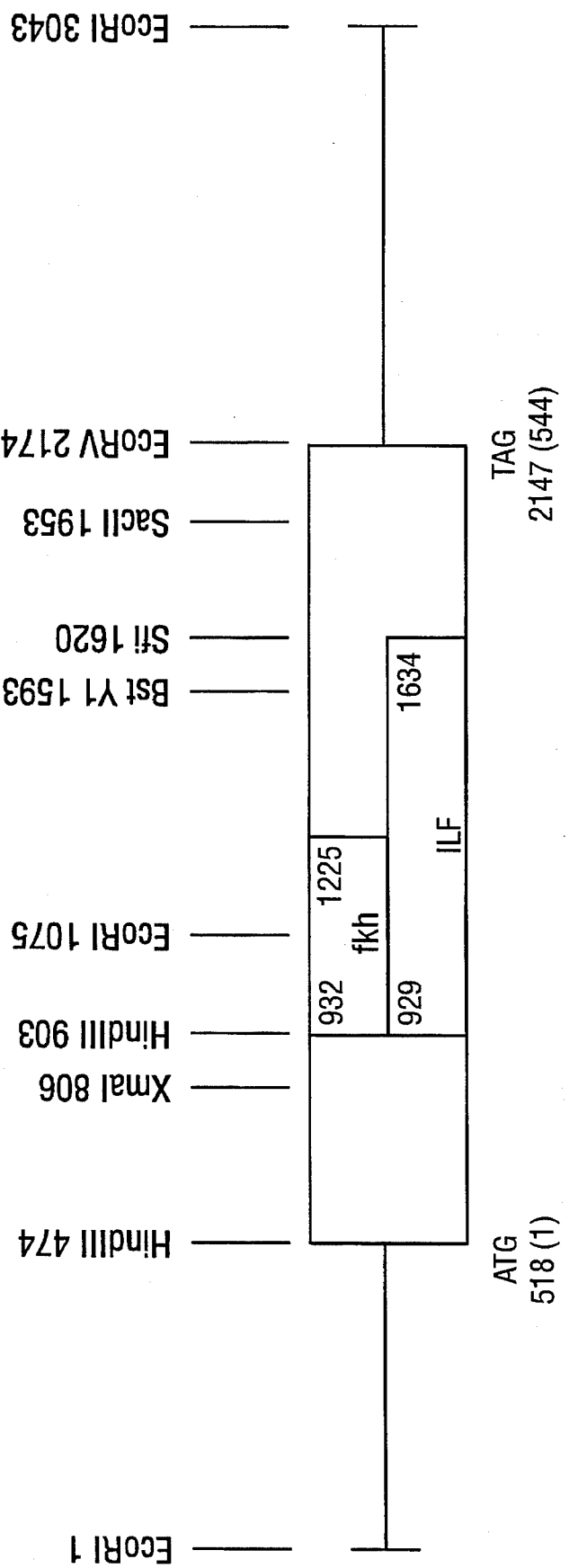
FIG. 3. Amino acid sequence of the ILF coding region. (A) A 543 amino acid open reading frame encoded by a portion of the ILF cDNA. The shaded region indicates the region of homology of ILF with the fork head and HNF-3A DNA binding domains. The circled region (GAGSSG) SEQ ID NO:12 contains homology with a nucleotide binding sequence, the boxed region (RKRRPR) SEQ ID NO:13 contains a potential nuclear localization signal, the underlined sequence (RTPLGPLSS) SEQ ID NO:14 is homologous to a region required for ubiquitin-mediated degradation, and the dotted line (NGT) indicates a potential N-glycosylation site. (B) The 3.0 kb ILF cDNA and the position of the 1629 bp open reading frame. The nucleotides (929 to 1634) in the original ILF cDNA and the region of homology with the fork head DNA binding (932 to 1225) are indicated, as are the positions of restriction sites in the ILF cDNA.

The present invention is directed to the cloning of a gene which encodes a cellular factor (ILF) that binds to NFAT-like motifs in an HIV-LTR. λgt11 expression cloning, using oligonucleotides which corresponded to such binding motifs, was used to successfully clone the gene designated herein as encoding an interleukin binding factor (ILF). This cDNA clone disclosed herein encodes a ubiquitously expressed 60 kD protein, herein termed interleukin enhancer binding factor (ILF). ILF binds specifically to purine rich motifs in the HIV-LTR. This factor also binds to similar purine-rich motifs in the interleukin-2 (IL-2) promoter, although with lower affinity than to HIV-LTR sequences. Northern blotting analysis reveals that this factor is constitutively expressed in both lymphoid and non-lymphoid cells. ILF is therefore a ubiquitous cellular factor that may potentially bind to similar purine-rich motifs in many cell types.

Analysis of the ILF gene isolated by the present inventors reveals that it is capable of giving rise to a number of different gene products by alternative splicing. One of these gene products is about 60 kDa protein. The other gene product that has been completely characterized is a 55 kDa. Other products of 70 kDa and products of molecular weight less than 55 kDa seem highly likely. The DNA binding domain of each of these gene product species has been found to have strong homology with a 98 amino acid region found in both the Drosophila fork head protein and in the gene family of hepatic nuclear factors known as HNF-3. The Drosophila fork head gene is involved in the regulation of terminal development in the Drosophila embryo (Weigel et al., 1989), while the HNF-3 gene family is predominantly expressed in cells that derive from the lining of the primitive gut (Lai et al., 1991). The binding sites of the fork head protein to Drosophila promoters has not yet been defined, while members of the HNF-3A have been demonstrated to bind and activate gene expression from important regulatory elements of the transethyretin and α-1 antitrypsin genes which are required for hepatocyte-specific gene expression (Costa et al., 1989). The sequences to which HNF-3A binds do not have a high degree of homology to the purine-rich sequences found in the HIV-LTR and IL-2 promoter.

In addition, ILF contains amino acid motifs that may function in nuclear localization, nucleotide specificity binding, and N-glycosylation. ILF also contains a nine amino acid motif with strong homology to that found in cyclin. Cyclin is known to mediate protein degradation by ubiquitin (Glotzer et al., 1991). A similar motif found in the yeast α2 repressor may mediate the in vivo degradation of this protein. Thus, it is believed that the activation of T-lymphocytes results in the degradation of ILF protein followed by subsequent binding of other cellular proteins such as NFAT, to these purine-rich motifs with resultant increases in gene expression.

Cotransfection studies presented here demonstrate that ILF play an important role in regulating both IL-2 and HIV gene expression. ILF is shown to exhibit specific binding to two homologous elements between −283 and −195 in the HIV-LTR and to activate an HIV-LTR (−342) CAT construct containing both elements, when cotransfected with the viral transactivator tat. ILF was found to activate IL-2 gene expression maximally when transfected at low concentrations, with a relative decrease in promoter activity at high concentrations. High ILF concentrations may decrease promoter activity by the phenomenon of "squelching." Squelching is a term used to describe the phenomenon whereby interactions between transcriptionally active promoter-bound ILF and putative transcriptional coactivators are inhibited by free unbound ILF. Alternatively, ILF may have different biological properties at different concentrations.

The inventors' studies of ILF gene expression have revealed several interesting results. Using the polymerase chain reaction (PCR), the inventors have established that ILF is expressed in a number of cell lines and tissue types. Additionally, the inventors have found that ILF mRNA transcripts are alternatively processed in a tissue specific manner. These alternatively processed mRNAs may have functional significance, particularly in regard to neoplastic lymphoid disorders.

The inventors also demonstrate herein that ILF is capable of inhibiting gene expression directed by the HIV-LTR in both resting and stimulated T-lymphocytes. This data supports the proposition that the presence of high levels of ILF is involved in maintaining the latent state of HIV. The mechanism involved in ILF repression of the IL-2 promoter and the HIV-LTR remains unclear. However, while not intending to be limited to any particular mechanism of action or function of the present invention, the inventors postulate that ILF may act by competing for binding to NFAT sites in the IL-2 promoter and the HIV-LTR with a variety of other cellular proteins which are capable of activating gene expression. Alternatively, ILF may contain domains which function in transcriptional repression, either directly or by interaction with additional cellular proteins. It is also possible that both of these mechanisms may be responsible for repression by ILF.

Gene expression during early T-cell activation is regulated by a complex array of stimuli which act via the signal transduction pathway. In addition to activation of specific classes of cellular genes during T-cell stimulation, the silencing of these genes by cellular factors is also likely critical for control of T-cell function. This complex pattern of gene regulation is mediated by multiple regulatory elements which serve as binding sites for both positive and negative acting cellular factors. The present invention demonstrates an interaction of the ILF which mediates transcriptional repression, via a critical regulatory motif in the IL-2 promoter and the HIV-LTR.

ILF is abundantly expressed in T-cells. This factor, together with the inventors' demonstration of the ability of ILF to stimulate IL-2 gene expression, supports the important role of ILF in regulating T-cell activation. T-cell activation is also postulated by the present inventors to play an important role in progression from latent HIV infection to full-fledged AIDS. The data presented herein by the inventors support the prophesied use of the ILF protein to prevent T-cell activation and the resulting immune system pathologies and lymphokine deficiencies which may result. Alternatively, specific inhibition of the ILF may be used to prevent T-cell activation related expression of the HIV virus, providing a potential novel method for treating and inhibiting HIV infection and AIDS.

The inventors' identification, cloning and characterization of ILF is therefore an important step towards an understanding of both immune function and HIV pathogenesis. As such, ILF or ILF-like molecules have great potential as a therapeutic agents. The inventors contemplate that such agents may function clinically as therapeutically active derivatives of ILF, or alternatively, as enhancers or repressors of endogenous ILF expression.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

CLONING OF A CELLULAR FACTOR ILF

The present example is provided to demonstrate the method used to clone a cellular factor designated ILF which was found to bind particular NFAT-like motifs in the HIV-LTR.

1. Identification of the ILF Gene

The ILF gene was identified by screening HeLa, B cell, and Jurkat λgt11 cDNA libraries (obtained commercially from Clontech Laboratory, Inc.) as described (Weigel & Jackle, 1990). Radio [$^{32}$P]-labelled wild-type and mutant double-stranded ligated oligonucleotide probes were used to screen these. The sequence of these wild-type oligonucleotides correspond to portions of the HIV-LTR (Tong-Starksen et al., 1987). These extend from the bases shown below and have the following sequences:

(HIV-1 LTR) −283 to −256 (distal ILF motif): 5'-GAAGAGGCCAATGAAGGAGAGAACAACA-3' SEQ ID NO: 15

−223 to −195 (proximal ILF motif): 5'-GAGGACGCGGAGAAAGAAGTGTTAGTGTG-3' SEQ ID NO: 16

The sequence of the mutant oligonucleotides for the distal ILF motif are: 5'-GTCGTGGCCTCTGTCTAGTGTGGCAACA-3' SEQ ID NO: 17. Positive phage were subsequently purified and screened in tertiary platings. A 706 bp fragment which contained the ILF DNA binding domain was labeled by random priming and used to screen a human HeLa cDNA lambda ZAP library (Stratagene) to identify full-length cDNA clones. DNA sequence analysis of these clones employed the Sanger method with the SEQUENASE® system (United States Biochemical).

2. Construction of Glutathione S-Transferase/ILF Fusion Proteins

A 1.3 kb XmaI/EcoRV fragment extending from nucleotides 807 to 2174 in the ILF cDNA was first cloned into the same sites of the Bluescript vector (Ausbabel et al., 1987). The recombinant plasmid was digested with BamHI and EcoRV for in-frame subcloning into the BamHI and SmaI sites of pGEX-3X (Pharmacia) (Smith & Johnson, 1988) to express a glutathione-S-transferase/ILF fusion protein of 72 kD (ILFΔ1). ILFΔ2 was constructed by insertion of an XmaI/SfiI fragment extending from nucleotides 807 to 1620 into pGEX-3X, giving a 58 kD fusion protein. ILFΔ3 was constructed by inserting an XmaI/EcoR1 fragment extending from nucleotides 807 to 1075 into pGEX-3X, yielding a 37 kD fusion protein.

3. Gel Retardation Analysis

Double-stranded oligonucleotides used in gel retardation analysis (Muchardt et al., 1990) correspond to the two ILF motifs in the HIV-LTR between −283 and −256 (distal) and between −223 and −195 (proximal) (Tong-Starksen et al., 1987), the NFAT motif in the IL-2 promoter between −285 and −254 (Shaw et al., 1988), an AP1 binding site in the adenovirus early region 3 promoter between −103 and −83 (20), and a CREB binding site in the somatostatin promoter extending from −60 and −33 (Montminy et al., 1986). The sequences are as follows:

IL2/NFAT: 5'-AATTGGAGGAAAA SEQ ID NO: 18-ACTGTTTCATACAGAAGGCGT-3' SEQ ID NO: 19;

CREB/ATF: 5'-GGTTCCTCCTTGGCTGACGT SEQ ID NO: 20-CAGAGAGAGA-3' SEQ ID NO: 21;

AP1: 5'-GAAGTTCAGATGACTAACTCA-3' SEQ ID NO: 22.

A 56 nucleotide AluI fragment extending from −310 to −255 in the HIV-LTR was also isolated and end-labeled for use in gel retardation assays. β-galactosidase/ILF fusions were prepared as described (Ausbabel et al., 1987) and purified with monoclonal anti-β-galactosidase chromatography (Promega). Glutathione S-transferase fusion proteins were purified with affinity chromatography as described (Muchardt et al., 1990). Fusion proteins were detected using rabbit polyclonal antibody raised to trypE-ILF fusion proteins and monoclonal anti-β-galactosidase antibody using Western blot analyses.

4. Isolation of cDNA Clones Encoding ILF

To clone genes encoding cellular factors which bind to purine-rich motifs in the HIV-LTR, modifications of the λgt11 expression cloning procedure (Singh et al., 1988) were used. The homology of these sequences to related purine-rich regions found in other viral and cellular promoters discussed herein are shown in Table 1. Oligonucleotides extending from either −283 to −256 or −223 to −195 in the HIV-LTR, referred to hereafter as the distal and proximal ILF motifs respectively, were ligated and used to probe λgt11 cDNA libraries prepared from either HeLa or lymphoid (B cell or Jurkat) RNA. Several isolates were identified from each of these libraries which specifically bound to both of the ILF motifs but not to mutated oligonucleotides. Each of these isolates contained regions of identical amino acids homologous to the so-called fork head DNA binding domain (Weigel & Jackle, 1990). One of these cDNAs, ILF, isolated from a λgt11 HeLa cDNA library was further characterized.

5. ILF binds to related sequences in the HIV-LTR and IL-2 promoter

TABLE 1

Related Sequence Motifs in HIV and IL-2 Promoters
SEQ ID NO: 7, 8, 9, 10 and 11 respective

| IL-2: | -291 | A | G | A | A | A | G | G | A | G | G | A | A | A | A | -277 |
| HIV distal: | -276 | C | C | A | A | T | G | A | A | G | G | A | G | A | G | A | -260 |
| HIV prox: | -221 | G | A | C | G | C | G | G | A | G | A | A | A | G | A | A | -206 |
| MHC: | -70 | C | C | A | A | G | T | G | A | G | G | A | A | C | C | A | -56 |
| SV40 PU box: | -319 | C | T | G | A | A | A | G | A | G | G | A | A | C | T | T | -305 |

To characterize the β-galactosidase/ILF fusion protein produced from the λgt11 HeLa cDNA isolate, lysates were prepared from phage-infected *E. coli* and purified by anti-β-galactosidase Sepharose chromatography (FIG. 1A, lanes 3 and 4). In addition, β-galactosidase produced from λgt11 phage not containing a cDNA insert was purified by anti-β-galactosidase Sepharose chromatography used as a control (FIG. 1A, lanes 1 and 2). The β-galactosidase protein migrated at ~110 kD whereas the β-galactosidase/ILF fusion protein migrated at 135 kD (FIG. 1A, lanes 2 and 4). Some breakdown of the β-galactosidase occurred in these samples resulting in several lower molecular weight species of between 70–90 kD. To further characterize these proteins, Western analysis was performed with antibody generated to either β-galactosidase (FIG. 1B) or ILF (FIG. 1C). Both β-galactosidase and β-galactosidase/ILF were reactive with anti-β-galactosidase (FIG. 1B, lanes 1 and 2), while only the β-galactosidase/ILF fusion protein was detected with anti-ILF (FIG. 1C, lanes 1 and 2).

Gel retardation analysis with either the β-galactosidase protein or the β-galactosidase/ILF fusion protein was then performed with an end-labeled HIV-LTR fragment extending from −310 to −255. The β-galactosidase/ILF fusion protein was found to bind to the HIV-LTR probe (FIG. 2, lane 3), whereas the β-galactosidase protein did not bind under identical conditions (FIG. 2, lane 2). Competition analysis was performed to demonstrate the specificity of this binding. Oligonucleotides corresponding to either the distal ILF motif in the HIV-LTR (FIG. 2, lanes 4 and 5) or the NFAT motif in interleukin-2 promoter (FIG. 2, lanes 6 and 7) were found to specifically compete with the binding of the β-galactosidase/ILF protein. Likewise, the proximal ILF motif in the HIV-LTR also resulted in complete competition of ILF protein binding. However, in a number of different experiments, both the proximal and distal HIV motifs were noted to serve as better competitors for ILF binding than the NFAT motif. Oligonucleotides corresponding to either AP1 (FIG. 2, lanes 8 and 9) or CREB (FIG. 2, lanes 10 and 11) binding sites did not compete for the binding of ILF. These results demonstrated that ILF binds specifically to related purine-rich sequences in the HIV-LTR and IL-2 promoter.

6. ILF Contains a Fork Head DNA Binding Domain

A fragment containing the ILF DNA binding domain was used as a probe to attempt to isolate full length cDNAs from a HeLa cDNA library. A 3.0 kb cDNA was isolated and the sequence of this clone between nucleotides 929 to 1634 was identical to that of the probe. RNase T2 protection studies of either HeLa or Jurkat mRNA using different portions of the 3.0 kb cDNA as probes demonstrated the integrity of this clone, which was also confirmed by Southern blotting analysis. An open reading frame of 543 amino acids, which extended from a potential initiating methionine at nucleotide 518 to a stop codon at nucleotide 2147, was identified. In vitro translation of ILF RNA in rabbit reticulocyte lysate yielded a 60 kD species. There was a stop codon 138 nucleotides upstream of the methionine and the homology to a consensus Kozak sequence suggested that an initiating methionine was present (Kozak, 1983). The amino acid sequence of this open reading frame, termed ILF-1, and a restriction map of the cDNA were determined (FIG. 3).

Comparison of the amino acid sequence of ILF with other amino acid sequences from GenBank revealed certain homologies. The ILF cDNA is now in GenBank under accession number M94654. Homologies were found between a 98 amino acid region of ILF and both the Drosophila regulatory protein, fork head (Weigel et al., 1989), and the DNA binding domain of the hepatocyte specific factor, HNF-3A (Lai et al., 1990). Within this region of ILF and fork head, there was 46% amino acid identity and 81% homology, allowing for conservative amino acid changes. The region of homology between ILF, fork head, and HNF-3A is shown in FIG. 4. A number of other conserved amino acid motifs were also noted (FIG. 4). These include a potential nuclear localization signal (RKRRPR) SEQ ID NO: 13 (Burglin & De Robertis, 1987), a sequence (GAGSSG) SEQ ID NO: 12 with homology to a nucleotide binding site found in a number of enzymes including the ras oncogene (Wierenga & Hol, 1983), a potential ubiquitin-mediated degradation signal (RTPLGPLSS) SEQ ID NO: 14 (Glotzer et al., 1991), and a potential N-glycosylation site (NGT). It was also noted that ILF contained a high content of several amino acids including proline (11%), serine (9.6%) and threonine (7.7%). Thus, ILF contains amino acid motifs consistent within other cellular transcription factors.

7. Deletion of the ILF Fork Head Domain Eliminates DNA Binding

To determine the region of the ILF protein which was required for DNA binding, deletions were placed into the isolated ILF cDNA. These ILF deletion constructs were fused to the glutathione S-transferase gene in the bacterial expression plasmid pGEX-3X. This expression plasmid is described in Smith & Johnson (1988), which reference is specifically incorporated herein by reference for such purpose. The pGEX expression system was used to facilitate the purification of glutathione S-transferase fusion proteins using glutathione-agarose affinity chromatography.

The constructs tested included a deletion of the amino terminus of ILF, a deletion of both the amino and carboxyl termini of ILF, or a deletion of the fork head domain in addition to the amino and carboxyl termini of ILF. Oligonucleotides corresponding to the distal ILF site in the HIV-LTR, the NFAT site in the IL-2 promoter, and an HIV-LTR fragment containing the distal ILF site were used in gel retardation analysis.

Figure 5C:
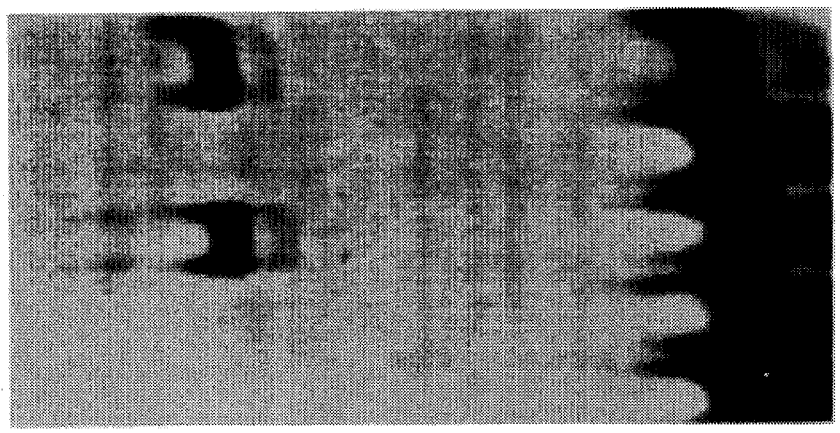
FIG. 5. Gel retardation analysis of glutathione S-transferase/ILF fusions. Gel retardation analysis was performed with either ILF oligonucleotides (A), a fragment extending from −310 and −255 in the HIV-LTR (B), or NFAT oligonucleotides (C) and 4 μg of each of the glutathione S-transferase/ILF fusions. Lane 0, probe alone; lane 1, glutathione S-transferase (GST) protein alone; lane 2, a deletion of both the amino and carboxyl-termini in the GST/ILF fusion (ΔILF3); lane 3, a deletion of the ILF fork head DNA binding domain in addition to the amino and carboxyl termini in the GST/ILF fusion (ΔILF2); lane 4, an amino-terminal deletion of ILF in the GST/ILF fusion (ΔILF1).
Figure 5B:
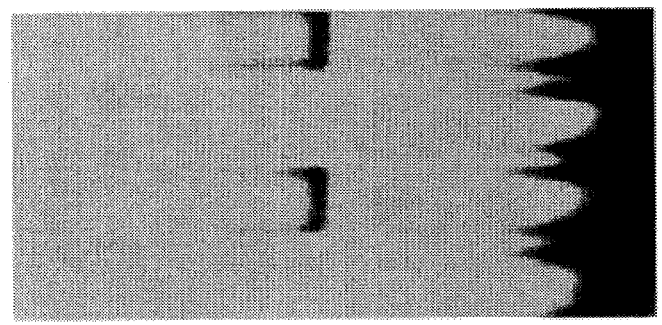
Figure 5A:
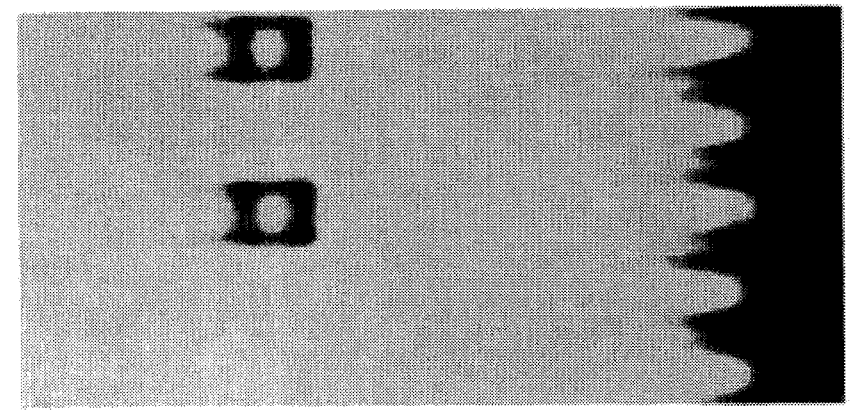

No binding of the purified glutathione S-transferase protein to any of the above-described probes was observed (FIG. 5, lane 1). Deletion of portions of both the amino and the carboxyl-termini of ILF resulted in a protein that retained specific binding to all these probes (FIG. 5, lane 2). Deletion of the fork head binding domain in addition to the amino and carboxyl termini of ILF resulted in a protein which did not bind to any of these probes (FIG. 5, lane 3). A deletion of the amino-terminus of ILF resulted in specific binding to all three probes (FIG. 5, lane 4). The binding specificity of each of these proteins was similar using the proximal ILF binding site. These results implicate the fork head domain in the DNA binding properties of ILF to the HIV-LTR and the IL-2 promoter. These results also demonstrate that the fork head domain was sufficient to confer the binding specificity of the ILF protein to the NFAT binding sites.

EXAMPLE 2

REGULATION OF HIV AND IL-2 GENE EXPRESSION BY ILF

In order to demonstrate the effects of ILF on HIV and IL-2 gene expression and its overall role in T lymphocyte activation, in vivo transient transfection experiments using the Jurkat T-cell leukemia line were performed. The present example also demonstrates the utility of using ILF and ILF-like proteins for inhibiting HIV gene expression and for stimulating IL-2 gene expression.

1. Cotransfection Assays

ILF was cloned into the eukaryotic expression plasmid PDP and was tested in cotransfection assays with either IL-2 Promoter chloramphenicol acetyltransferase (CAT) or HIV-1 LTR CAT reporter constructs. Jurkat cells were transfected by electroporation (1180 μF, 250 V) and were grown in RPMI medium (10% fetal calf serum (FCS), 100 units/ml penicillin, 100 mg/ml streptomycin). The cells were fed with fresh medium 24 hours after transfection and were harvested 32 hours post-transfection. Whole cell extracts were prepared from the harvested cells and were assayed for CAT activity.

2. CAT Assays

Transfected Jurkat cells were ($5 \times 10^6$ to $10^7$ cells) were harvested by centrifugation at 3000 rpm. The cell pellet was resuspended in 100 μl of 0.25M tris pH 8.0 and subject to three rounds of freezing and thawing. Incubation of extract with $^{14}C$ chloramphenicol and acetyl CoA was performed for 1 hr. as described followed by thin layer chromatography and autoradiography.

Figure 6:
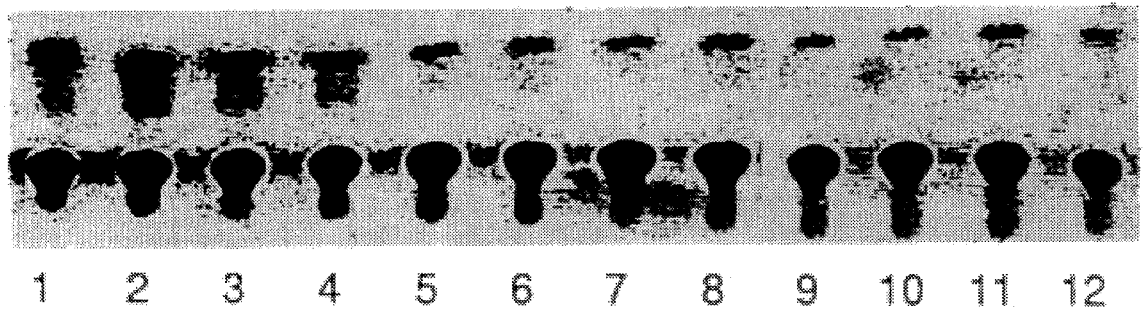
FIG. 6. Varying concentrations of PDP-ILF were cotransfected with an IL-2 (−342) CAT construct containing 342 base pairs of IL-2 promoter sequence 5' to the transcription start site. Cotransfection of 1 μg of PDP 18-ILF and 5 μg of IL-2 (−342) CAT yielded 8.84% conversion of non-acetylated chloramphenicol to acetylated forms, which represents a greater than three-fold increase over baseline promoter activity (no ILF transfected). Transfection of increasing amounts of ILF (2.5 μg, 5.0 μg) resulted in greater than baseline promoter activity but decreased activity relative to transfection of 1.0 μg of PDP-ILF. Contrastingly, cotransfection of varying amounts of PDP-ILF with IL-2 (−240) CAT and IL-2 (−143) CAT constructs did not alter promoter activity.

Varying concentrations of PDP-ILF were cotransfected with an IL-2 (−342) CAT construct containing 342 base pairs of IL-2 promoter sequence 5' to the transcription start site (FIG. 6). Cotransfection of 1 μg of PDP 18-ILF and 5 μg of IL-2 (−342) CAT yielded 8.84% conversion of non-acetylated chloramphenicol to acetylated forms, which represents a greater than three-fold increase over baseline promoter activity (no ILF transfected). Transfection of increasing amounts of ILF (2.5 μg, 5.0 μg) resulted in greater than baseline promoter activity but decreased activity relative to transfection of 1.0 μg of PDP-ILF. Contrastingly, cotransfection of varying amounts of PDP-ILF with IL-2 (−240) CAT and IL-2 (−143) CAT constructs did not alter promoter activity.

Figure 7:
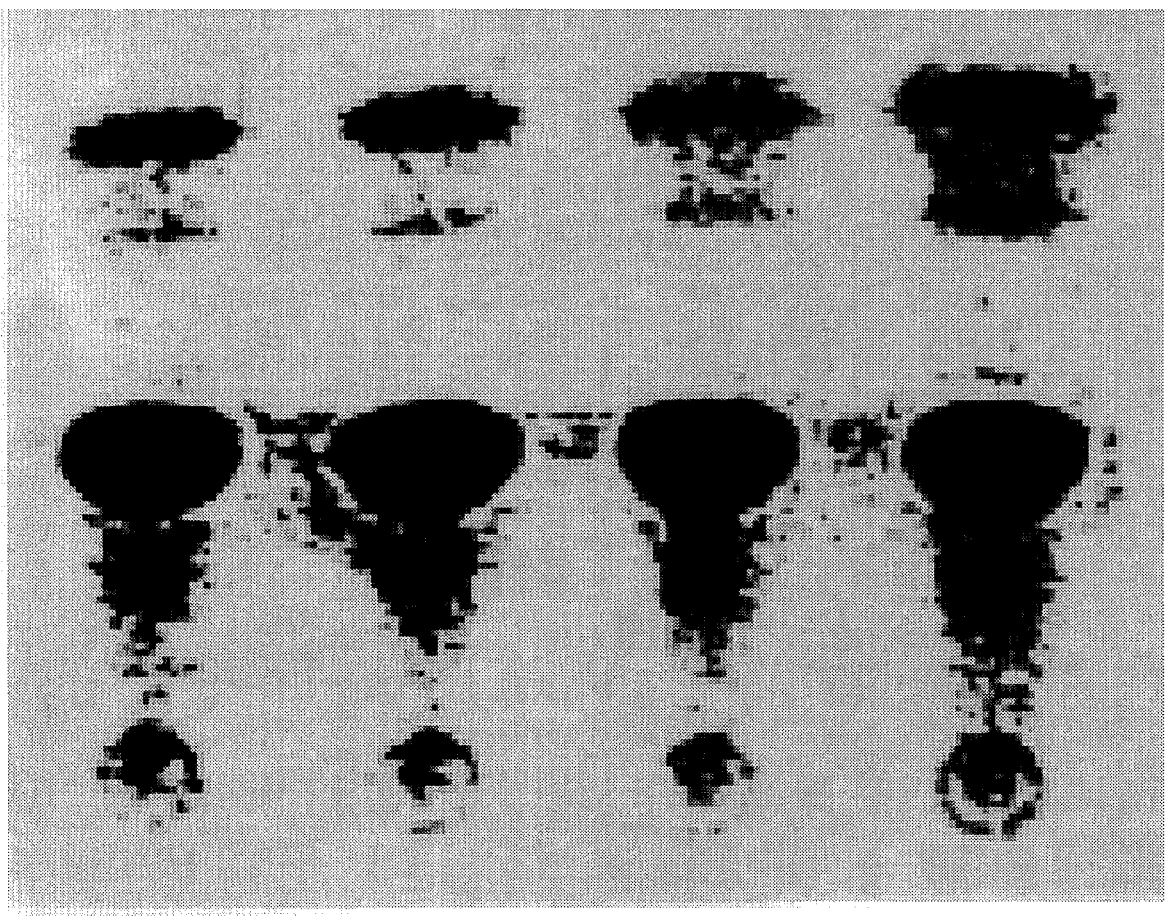
FIG. 7. Cotransfection of increasing amounts of PDP-ILF with HIV LTR (−342) CAT and PDP- Tat results in a progressive enhancement of HIV-LTR promoter activity. Transfection of 3 μg of PDP-ILF yielded approximately four-fold HIV-LTR activation when compared to baseline.

Cotransfection of increasing amounts of PDP-ILF with HIV-LTR (−342) CAT and PDP- Tat results in a progressive enhancement of HIV-LTR promoter activity (FIG. 7). Transfection of 3 μg of PDP-ILF yielded approximately four-fold HIV-LTR activation when compared to baseline.

The above results demonstrate that ILF plays an important role in regulating both IL-2 and HIV gene expression. The inability of ILF to alter promoter activity of IL-2 (−240) CAT and IL-2 (−143) CAT constructs provides new insights into the role of ILF in IL-2 gene regulation. This result primarily implicates promoter sequences between −342 and −240 as necessary for mediating ILF's effects on IL-2 expression. ILF indeed shows specific binding to a purine-rich element between −286 and −257 known to be bound by NFAT and to be crucial in activating IL-2 expression. Sequences between −158 and −145 show strong homology to this element but do not appear to be important in activation of the IL-2 promoter by ILF.

EXAMPLE 3

NEGATIVE REGULATION OF IL-2 AND HIV-1 GENE EXPRESSION BY ILF

The present example demonstrates the utility of the described invention as a negative-acting gene expression regulatory factor.

1. Gel Retardation Assays

The ILF cDNA was cloned downstream of the glutathione-S-transferase (GST) gens in the prokaryotic expression vector pGEX- 3X, and the GST/ILF fusion protein was over-expressed in bacterial culture and affinity-purified by glutathione-agarose column chromatography as described above. Gel retardation was performed using the GST/ILF fusion protein and labeled oligonucleotides corresponding to the NFAT site in the IL-2 promoter, also according to the protocol described above. The sequence of the oligonucleotides used in the gel retardation assays include the IL-2 promoter NFAT site extending from −285 to −254 (1), the distal (2) and proximal (3) NFAT binding sites in the HIV-LTR extending from −283 to −256 and −223 to −194 respectively, the HNF-3A binding site extending from −107 to −92 in the transthyretin promoter (4) and an Ap-1 binding site extending from −102 to −83 in the adenovirus early region 3 promoter (5). The sequence of these oligonucleotides are shown below:

(1) 5'-AATTGGAGGAAAAACTGTTTCATACA-GAAGGCGT-3' SEQ ID NO: 23
(2) 5'-GAAGAGGCCAATGFAAGGAGAGAACAACA-3' SEQ ID NO: 24
(3) 5'-GAGGACGCGGAGAAAGAAGTGTTAAGTGTG-3' SEQ ID NO: 25
(4) 5'-TGGAGTTGACTAAGTCAATAATCAGAATGAG-3' SEQ ID NO: 26
(5) 5'-GAAGTTCAGATGACTAACTCA-3' SEQ ID NO: 27

2. Expression constructs

The expression construct contains the ILF cDNA extending from ATG 518 to TAG 2147 under the transcriptional control of the Rous sarcoma virus promoter (RSV). A simian virus 40 (SV40) polyadenylation signal was placed downstream to the target gene. the β-globin gene under the transcriptional control of the same pRSV promoter was used to normalized transfection. The complete and the differentially truncated human interleukin-2 promoter (IL-2) were isolated by polymerase chain reaction (PCR) using synthetic oligonucleotides corresponding to the 5' flanking sequence of the IL-2 gene as primers and HeLa DNA as template. A Sma I site was placed at the 5' end of the IL-2 gene at −342, −273, −240 and −72, respectively, while an Xho I site was placed at the 3' end of the IL-2 gene at +47. The PCR products were digested with SmaI and Xho I, and cloned into a CAT expression construct containing the corresponding restriction sites. Either a EcoRV/Hind III (−339 to +80) or an AvaII/Hind III (−158 to +80) fragment of the HIV-LTR were joined to the CAT gene to construct either the HIV-LTR/−339 CAT or HIV-LTR/−158 CAT construct respectively. The resulting reporter constructs were used in co-transfection experiments with the expression constructs containing either β-globin gene or the ILF cDNA.

3. Cell Stimulation

For differential analyses in stimulated and unstimulated cells, plasmid constructs were introduced by electroporation into Jurkat cells, as described below, and the cells were divided equally at 20 hours post-transfection. One half was left unstimulated while the other half was stimulated with phorbol 12-myristate 13-acetate (PMA), phytohemagglutinin (PHA), and a calcium ionophore, ionomycin (Flanagan et al., 1991). The cells were harvested at 8 hours post-stimulation and CAT assays were performed. Each of the transfection experiments described below was repeated at least three times and quantitated by radioanalytical imaging scanner, with similar results being obtained each time. A typical transfection experiment from each set is presented.

Jurkat E cells were maintained in RPMI 1640 media (Gibco) supplemented with 10% v/v fetal calf serum, 100 units/ml penicillin G and 100 units/ml streptomycin sulfate (complete RPMI 1640) in a 5% $CO^2$ incubator. Cells were fed with complete media one day before transfection. Ten to fifteen million cells in 0.25 ml of complete RPMI 1640 were electroporated with 10 μg of each plasmid unless indicated otherwise using a 250 volts, low resistance and 1180 mF fast electric shock (Cellporator, Gibco-BRL). Cells were suspended in 10 ml of RPMI 1640 immediately after electroporation and incubated at 37° C. At 20 hours post-transfection, cells were equally split into two halves. One half was left unstimulated while the other half was stimulated by phorbol 12-myristate 13-acetate (PMA, 50 ng/ml, phytohemagglutinin (PHA, 4 mg/ml) and ionomycin (2 mM) at 37° C. for 8 hours. Unstimulated and stimulated Jurkat cells were harvested at 28 hours post-transfection. Cell extracts were prepared and incubated with $^{14}C$-labeled chloramphenicol to determine the CAT activity. The acetylated and non-acetylated reaction products were separated by thin layer chromatography as described by Gorman et al. (1982). After autoradiography was developed, the chromatograms were quantitated by a radioanalytical imaging scanner (AMBIS).

Figure 8:
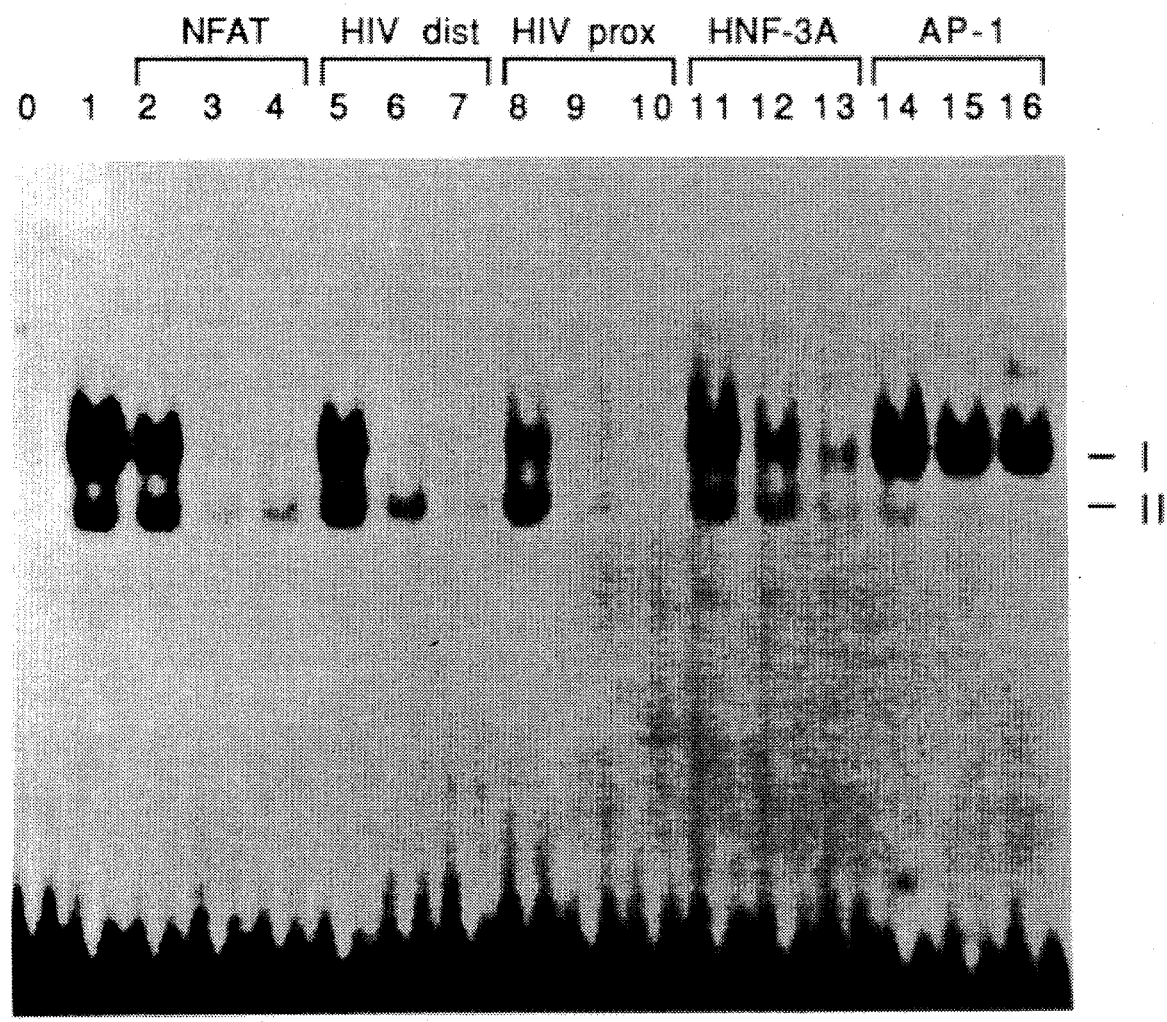
FIG. 8. Gel retardation of ILF with the IL-2 NFAT motif. (A) Oligonucleotides corresponding to the NFAT motif in the IL-2 promoter extending from −285 to −254 were end labeled with γP$^{32}$ATP and used in gel retardation analysis alone (lane 0), with glutathione-S-transferase (lane 1), or with a glutathione-S-transferase/ILF fusion protein (lanes 2–16). The specificity of binding was tested by competition with unlabeled oligonucleotides corresponding to the NFAT motif in the IL-2 promoter (lanes 2–4), sequences spanning −283 to −256 and −223 to −195 in the HIV-LTR which comprised distal (lanes 5–7) and proximal (lanes 8–10) NFAT motifs respectively, the hepatocyte nuclear factor HNF-3A binding site extending from −107 to −92 in the transthyretin promoter (lanes 11–13), and an AP-1 binding sequence extending from −103 to −83 in the early region 3 promoter (lanes 14–16). The unlabeled oligonucleotides were present in either an equimolar (lanes 2, 5, 8, 11, and 14), 5-fold (lanes 3, 6, 9, 12, and 15) or 20-fold (lanes 4, 7, 10, 13 and 16) molar excess of the labeled oligonucleotides. (B) Sequences of NFAT motifs in the IL-2 promoter and the distal and proximal regions of the HIV-LTR are shown.

ILF bound to oligonucleotides corresponding to the IL-2 NFAT site (FIG. 8, lane 2) while no detectable species was observed with glutathione-S-transferase alone (FIG. 8, lane 1). Two complexes I and II were noted; the major complex (I) was due to full-length GST/ILF while the lower complex (II) was due to GST/ILF degradation products. To determine the specificity of ILF binding, competition was performed with increasing concentrations of unlabeled related and nonrelated oligonucleotides. The sequences of these oligonucleotides are shown above. Oligonucleotides corresponding to the NFAT site in the IL-2 promoter (FIG. 8, lanes 2–4) or either of the two NFAT sites in the HIV-1 LTR (FIG. 8A, lanes 5–10), specifically competed the ILF species. There was some competition with oligonucleotides corresponding to an HNF-3 binding site (FIG. 8A, lanes 11–13), even though these oligonucleotides do not contain purine rich sequences similar to NFAT binding sites. However, this binding site interacts with a family of hepatocyte factors (HNF-3) whose fork head binding domains are homologous to that seen in ILF (Lai et al., 1990). Oligonucleotides corresponding to a binding site for the transcription factor AP-1 did not result in significant competition (FIG. 8A, lanes 14–16).

These results demonstrate that ILF binds specifically to NFAT-related binding motifs in the IL-2 promoter and the HIV-1 LTR. Since ILF bound specifically to the NFAT motif in the IL-2 promoter, the functional significance of this binding was not determined. The IL-2 promoter extending from −342 to +47 was placed upstream of the chloramphenicol acetyltransferase (CAT) gene, the construct was introduced by electroporation into Jurkat cells along with various amounts of a eucaryotic expression vector containing the ILF cDNA, as described above, and gene expression was analyzed.

In contrast to standard DEAE transfection protocols, the electroporation protocol used in these studies allowed the detection of significant levels of IL-2 CAT activity in both resting and stimulated Jurkat cells. This was especially critical for defining the regions of-the IL-2 promoter which could potentially interact with ILF.

Figure 9A:
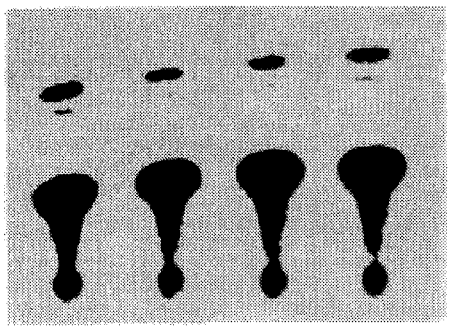
FIG. 9. ILF inhibits IL-2 gene expression. Jurkat cells were electroporated with 10 μg of an IL-2 CAT construct extending from −342 to +47 and increasing amounts of an eukaryotic expression construct pDP18 containing either β-globin (–) ILF (lanes 1–4) or the ILF cDNA (+) ILF (lanes 5–8). The amounts of the ILF expression construct are 0 (lanes 1 and 5), 2 μg (lanes 2 and 6), 5 μg (lanes 3 and 7) and 10 μg (lanes 4 and 8). Total amounts of DNA were normalized by addition of the pDP18 expression vector. Total amounts of DNA were normalized by addition of the pDP18 expression vector. At 20 hours post-transfection, the cells were equally divided. One-half was left unstimulated while the other half was stimulated with PMA (50 ng/ml), PHA (4 mg/ml) and ionomycin (2 mM) at 37° C. for 8 hours. Cells were harvested, extracts prepared, and CAT assays were performed by thin layer chromatography. The percent of $^{14}$C chloramphenicol conversion for each reaction is (A) (1) 2.5 (2) 1.5 (3) 1.7 (4) 3.1 (5) 1.8 (6) 1.1 (7) 0.8 (8) 0.7 and (B) (1) 27.1 (2) 27.5 (3) 22.5 (4) 23.5 (5) 23.8 (6) 14.0 (7) 9.0 (8) 4.5.
Figure 9B:
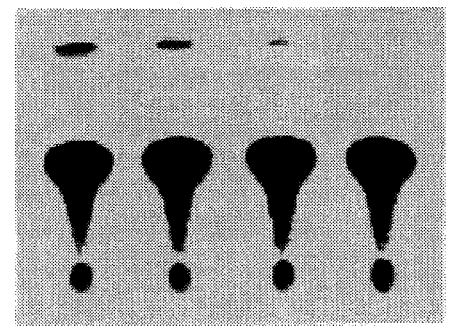
Figure 9C:
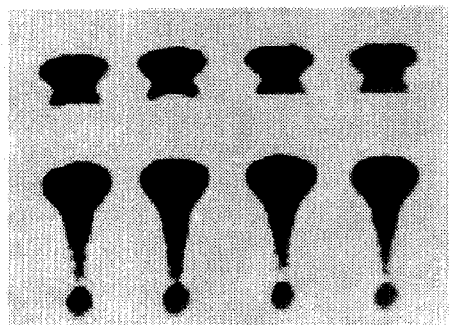
Figure 9D:
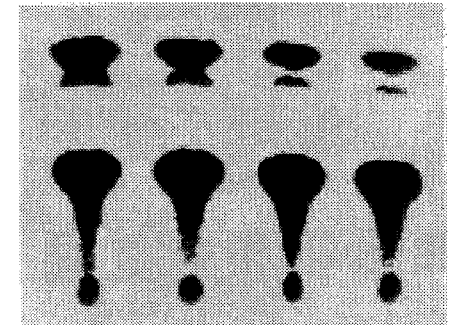

It was found that increasing concentrations of ILF resulted in decreased IL-2 gene expression in both unstimulated (FIG. 9A) and stimulated (FIG. 9B) Jurkat cells. At the highest concentration of ILF, the degree of inhibition of IL-2 gene expression was 2.5-fold in unstimulated (FIG. 9A, lane 8) and 5-fold in stimulated (FIG. 9B, lane 8) Jurkat cells, respectively. In three separate studies, the inhibition of IL-2 gene expression ranged from 2 to 4-fold in unstimulated Jurkat cells to 5 to 7-fold in stimulated cells. ILF did not repress the gene expression of other plasmids such as RSV-CAT which lacked NFAT binding sites.

The regulatory elements in the IL-2 promoter which mediated ILF repression were next examined. Several deletions were placed in the IL-2 promoter CAT construct (which extended from −342 to +47) such that most or all of the NFAT region was deleted (extending from either −273 or −240 to +47) or in addition, other upstream regulatory regions were also deleted (extending from −72 to +47) (3–5, 20, 21). Cotransfection of an ILF expression construct with the IL-2/−72 CAT construct into stimulated Jurkat cells resulted in no significant change in IL-2 CAT gene expression (FIG. 10, panel 1). Cotransfection of the ILF expression construct, with either the IL-2/−240 CAT or the IL-2/−273 CAT construct, both of which lacked the intact NFAT motif, did not result in significant inhibition of IL-2 gene expression (FIG. 10, panels 2 and 3, respectively). However, a 5-fold inhibition of IL-2 gene expression was noted with the complete IL-2/−342 CAT construct (FIG. 10, panel 4). Similar ILF inhibition of IL-2 CAT gene expression mediated by the NFAT motif was noted in unstimulated Jurkat cells. This demonstrated that ILF inhibition of IL-2 gene expression likely required the NFAT binding region which extends from −292 to −255 in the IL-2 promoter.

Figure 11A:
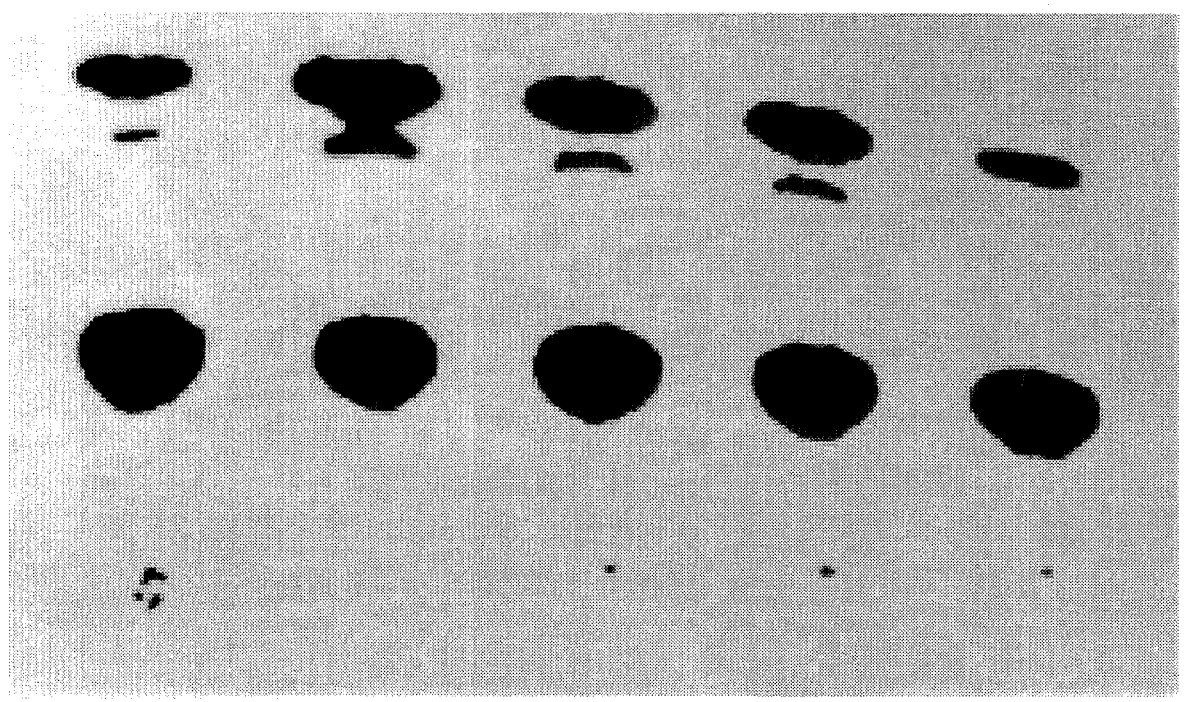
FIG. 11. ILF repression is mediated via interaction with the NFAT sites. (A) A chromatography showing CAT activity in extracts of transfected Jurkat cells stimulated with TPA, PHA, and cyclosporin. Jurkat cells were co-transfected by electroporation with 10 μg of CAT reporter and 10 μg of a eukaryotic expression construct containing the ILF cDNA. The CAT reporter constructs were either the IL-2/–342 CAT (lane 1), IL-2/–72 CAT (lane 2), or IL-2/–72 CAT continuing either one (lane 3), two (lane 4), or three (lane 5) NFAT motifs. The percent of $^{14}$C chloramphenicol conversion for each reaction is (1) 4.7 (2) 28.0 (3) 14.1 (4) 9.0 (5) 3.6. (B) A schematic representation of the IL-2 CAT constructs (extending from either –342 to +47) (lane 1), extending from –72 to +47 (lane 2) either one, (lane 3), two (lane 4) or three (lane 5) NFAT motifs placed upstream of the IL- 2 CAT construct are indicated (–72 to +47). The NFAT motifs are in the same orientation from 5' to 3'. The putative regulatory sites for NFAT, NFkB and anti-CD28 in the IL-2 promoter are indicated as are ovals for each NFAT motif and an arrow denoting the transcriptional start site for the IL-2 gene.

To even further demonstrate that ILF repression of IL-2 gene expression was mediated by the NFAT motif, either one, two or three copies of the NFAT motif were placed upstream of a truncated IL-2 CAT vector which extended from −72 to +47. Each of these constructs was cotransfected with the ILF expression construct into Jurkat cells followed by stimulation with PMA, PHA, and ionomycin (FIG. 11). A marked inhibition of expression from the IL-2 promoter CAT constructs was observed with increasing numbers of NFAT domains (FIG. 11, lanes 2–5). The maximal degree of inhibition was noted with three NFAT sites (FIG. 11, lane 5) where ILF resulted in a 7-fold inhibition of IL-2 gene expression as compared to no NFAT sites (FIG. 11, lane 2). These results were consistent with the studies described herein above, and further demonstrate that multiple NFAT binding sites are required for the function of these motifs.

Figure 12A:
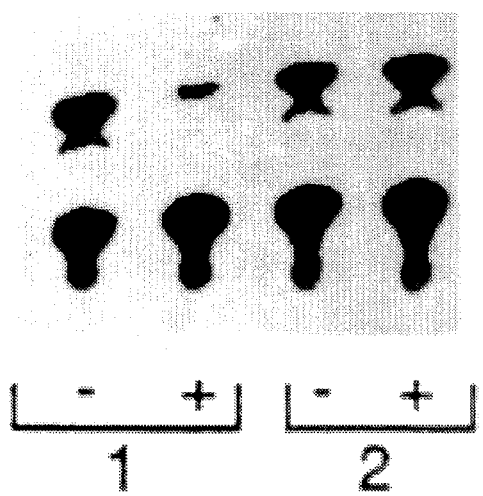
FIG. 12. ILF represses gene expression directed by the HIV-LTR. Thin layer chromatograms showing the HIV-LTR-directed CAT gene expression in extracts of transfected Jurkat cells either unstimulated (A) or stimulated with TPA, PHA and ionomycin (B). Jurkat cells were cotransfected by electroporation with 1 μg of an HIV-LTR CAT reporter construct and 10 μg of an eukaryotic expression construct containing either the β-globin gene (–ILF) or the ILF cDNA (+ILF). The CAT reporter constructs were either the HIV-LTR/–339 CAT construct containing two NFAT motifs (lane 1) or the HIV-LTR/–158 CAT construct which deleted the NFAT motifs (lane 2). The percent of $^{14}$C chloramphenicol conversion for each reaction is (A) (1–) 6.25 (1+) 0.77 (2–) 10.6 (2+) 23.4 and (B) (1–) 15.15 (1+) 0.64 (2–) 13.4 (2+) 17.6. (C) A schematic illustration of the HIV-LTR CAT reporter constructs. The HIV-LTR/–339 CAT construct contains the CAT gene directed by the HIV-LTR extending from –339 to +80, contains two NFAT motifs in the HIV-LTR. The HIV-LTR/–185 CAT construct extends from –158 to +80 in the HIV-LTR and deletes both NFAT sites. The distal (–276 to –262) and the proximal (–220 to –206) NFAT motif (in the HIV-LTR referred here as Dist ILF and Prox ILF) are indicated. The transcriptional start site of the HIV-LTR is denoted by an arrow.
Figure 12B:
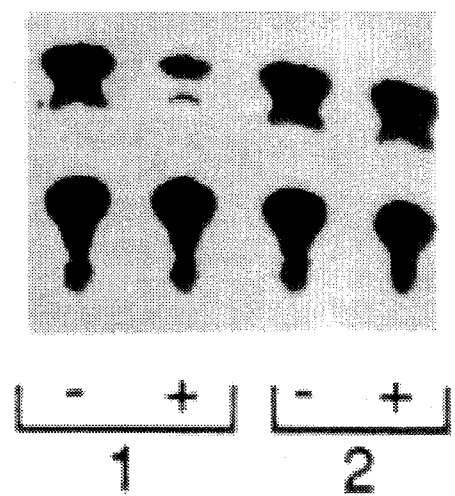
Figures 1, 2, 12C:
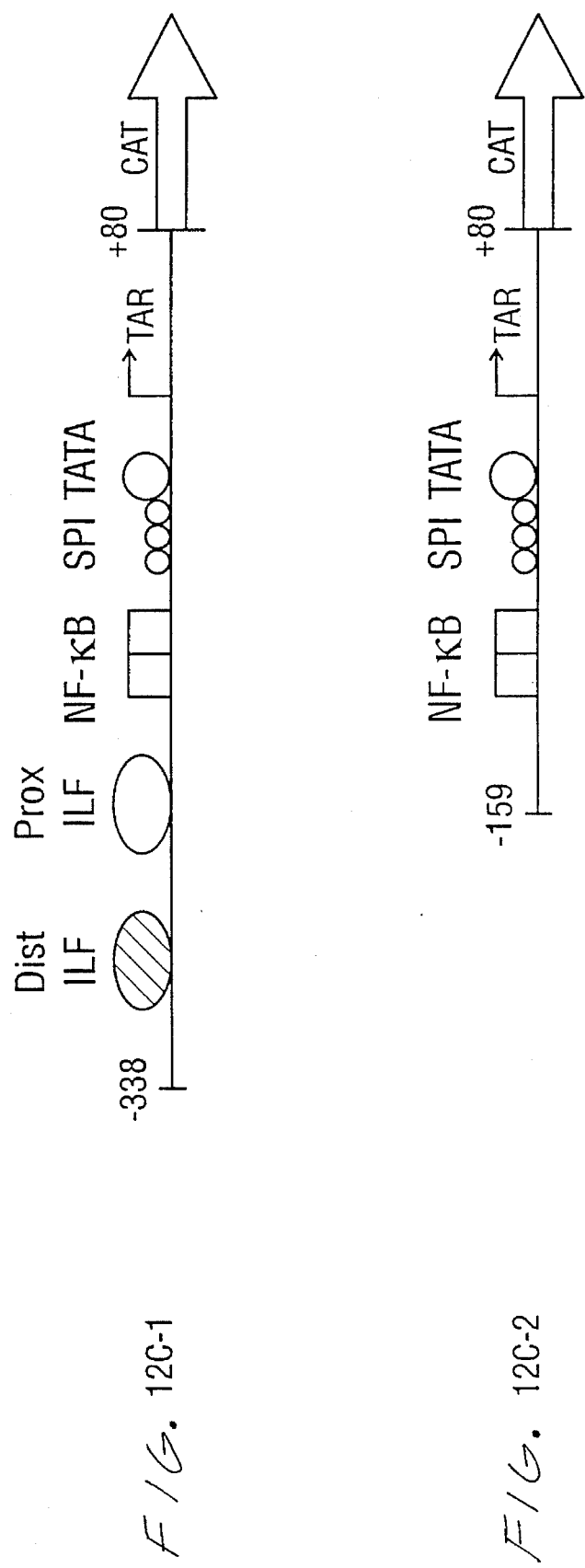

Since the NFAT motifs are also found in the HIV-1 LTR and gel retardation analysis revealed that ILF also bound specifically to these sites (FIG. 8, lanes 5–10), the effect of ILF on gene expression directed by the HIV-1 LTR was next examined. Either an HIV-1 LTR CAT construct extending from −338 to +80 which contained both proximal and distal NFAT sites or a similar construct extending from −159 to +80 which deleted both NFAT motifs were used in co-transfection experiments with ILF (Tong-Starksen et al., 1987; Siekevitz et al., 1987). ILF inhibited HIV-1 LTR CAT gene expression from the −338 construct from 3 to 7-fold in unstimulated (FIG. 12A, lane 1(−)) and from 5 to 20-fold in stimulated (FIG. 12B, lane 1(−)) Jurkat cells as compared to contransfection with a β-globin expression construct (FIGS. 12A and B, lane 1(+)). However, no significant inhibition by ILF was observed in both resting and stimulated Jurkat cells when co-transfection was performed using the HIV-1 LTR CAT construct which extended from −159 and deleted both of the NFAT-like motifs (FIG. 12A and B, lane 2). Similar inhibition of the −338 HIV-1 LTR CAT construct by ILF was seen in the presence of tat. These results demonstrated that ILF was able to inhibit gene expression likely by interacting with the NFAT motifs in the HIV-1 LTR.

A number of different transcription factor genes have been demonstrated to encode both positive and negative factors by alternative splicing of their mRNAs. Interestingly, the ILF gene generates a variety of different cDNAs and it is possible that both positive and negative factors may be derived from the ILF gene.

EXAMPLE 4

IDENTIFICATION OF ILF-2 cDNA

In Example 1, the isolation and partial characterization of a cDNA molecule encoding an ILF protein was reported. The following example is directed to the inventors' discovery of a further ILF-encoding cDNA, herein termed ILF-2.

Identification of different ILF cDNAs. A 706-bp portion of the ILF cDNA was identified using λgt11 expression cloning with wildtype and mutated double-stranded ligated oligonucleotides. This fragment was labeled by random priming and used to screen a HeLa cDNA ZAP library (Stratagene) in an attempt to identify full-length cDNA clones. DNA sequence analysis of these clones employed the Sanger method sequence system. PCR analysis (30 cycles) with HeLa poly(A)RNA (10 µg) was performed to conclusively establish the existence of alternative splicing of ILF mRNA. HeLa poly(A)RNA (10 µg) was reverse transcribed using random hexamer primers and was used as a template for PCR (40 cycles: 94° C., 1 min; 72° C., 1 min; 55° C., 1 min). The following sets of oligonucleotides were used as PCR primers.

Set 1:
Sense 5'-AGCTGATAGTTCAGGCGATT-3' SEQ ID NO: 28
Antisense 5'-ACAGAGTTGATATCGTTAAA-3' SEQ ID NO: 29
Set 2:
5'-AGGAGAATGGAGACCACAGGGAAGT-3' SEQ ID NO: 30
5'-CTGCTGTGTCAACTGAGGCA-3' SEQ ID NO: 31

Figure 13A:
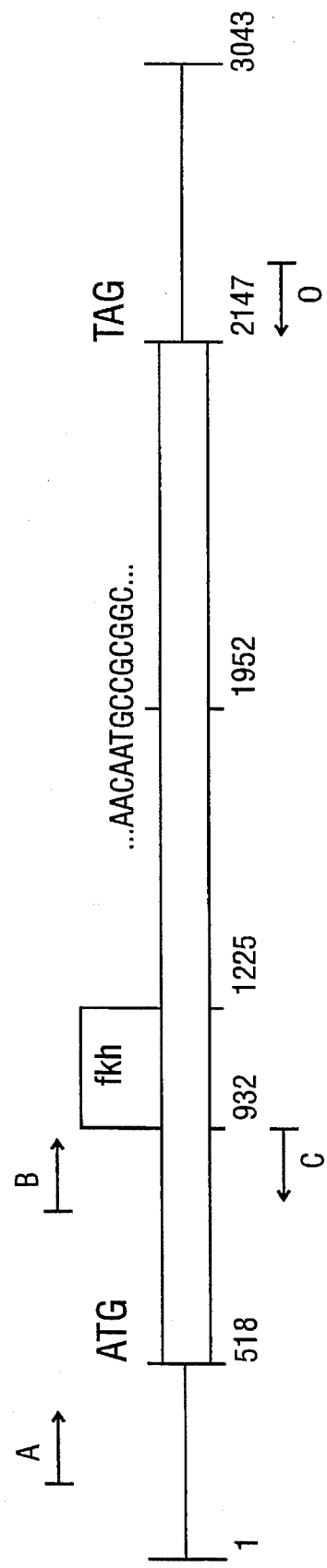
FIG. 13. Maps of the ILF clones. Schematic of ILF cDNAs. A schematic of two ILF cDNAs isolated from a HeLa cDNA library is indicated. The coding sequences are represented by shaded areas. In ILF-1, the coding sequence extends from nucleotide 518 to 2147. The sequence for ILF-2 is identical with IFL-1 from nucleotides 518 to 1952 but differs by insertion of a 422-bp fragment at this point, which introduces a stop codon at position 2009. The region of homology with the Drosphilia fork head gene is indicated.
Figure 13B:
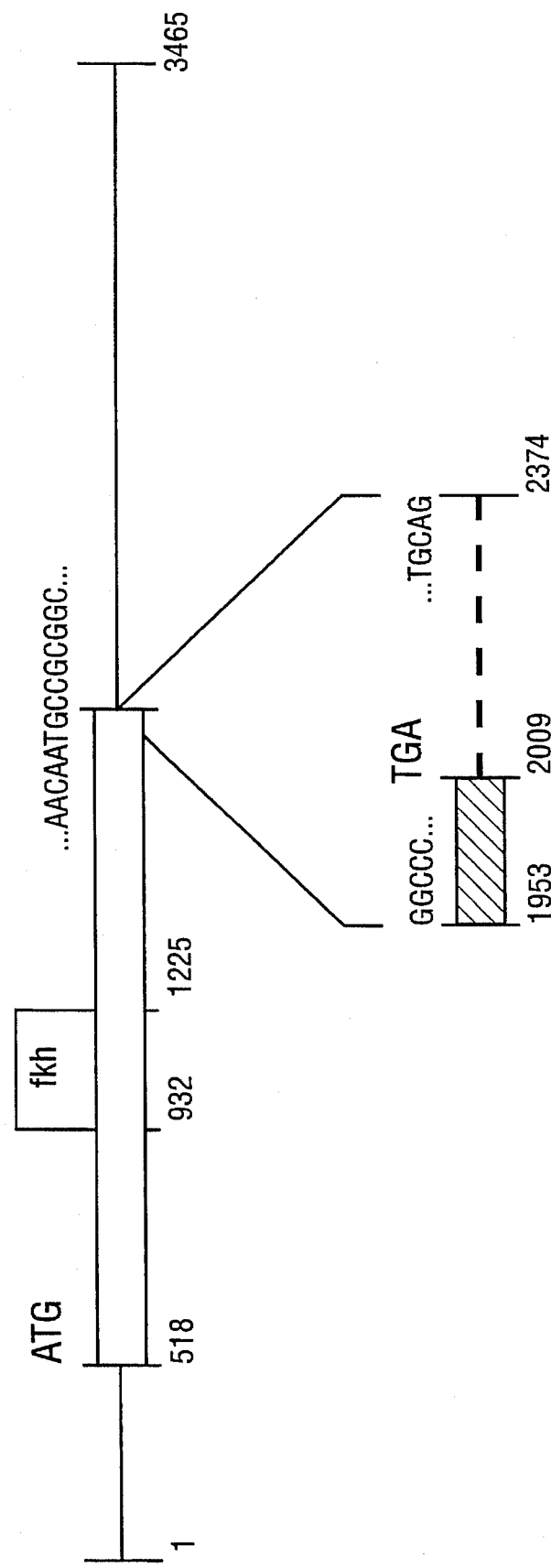
Figure 16C:
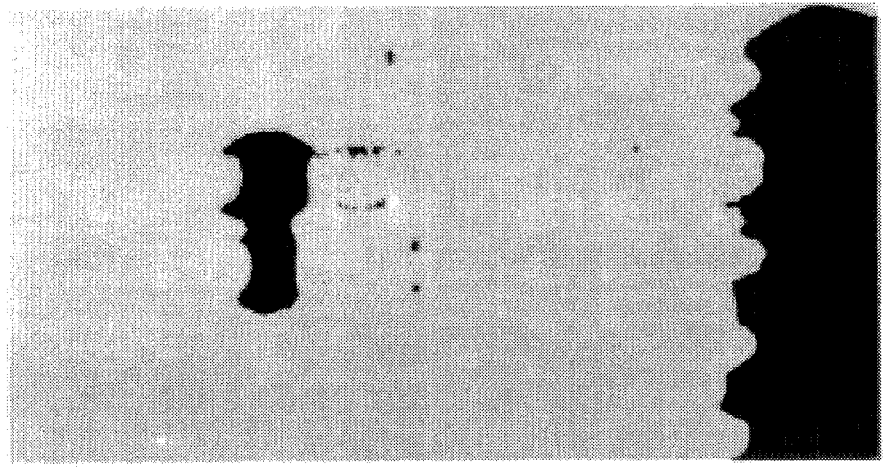
FIG. 16. Gel retardation analysis of ILF. Gel retardation was performed with labeled DNA probes corresponding to either (A) an HIV-1 LTR fragment extending from –310 to –265 (B) oligonucleotides corresponding to nucleotides –283 to –256 in the HIV-1 LTR or (C) oligonucleotides corresponding to nucleotides –285 to –254 in the IL-2 promoter. In A, B, and C, lane 1 contains no added extract, lane 2 contains glutathione-agarose-purified glutathione S-transferase (GST) alone, and lanes 3–5 contain similar purified GST/ILF-1 fusion proteins, with lane 3 containing a portion of the ILF protein extending nucleotides 903 to 1252, and lane 5 containing a portion of the ILF protein extending from nucleotide 807 to 1075.
Figure 16B:
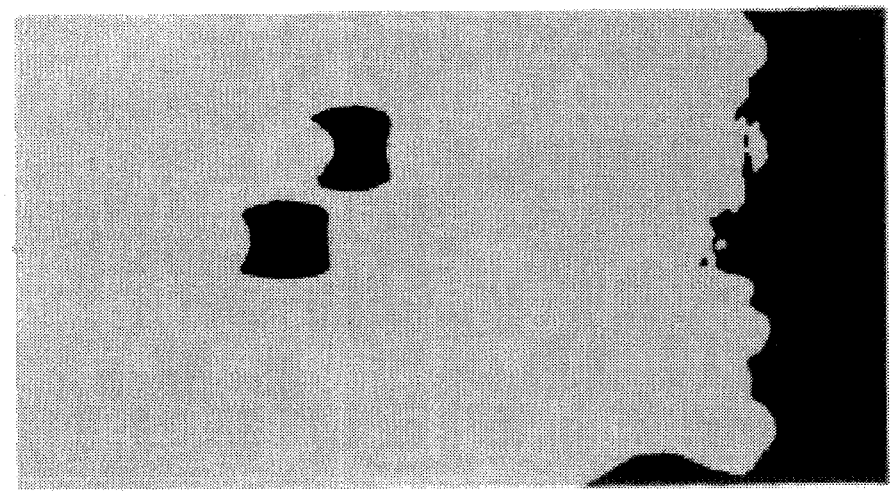
Figure 16A:
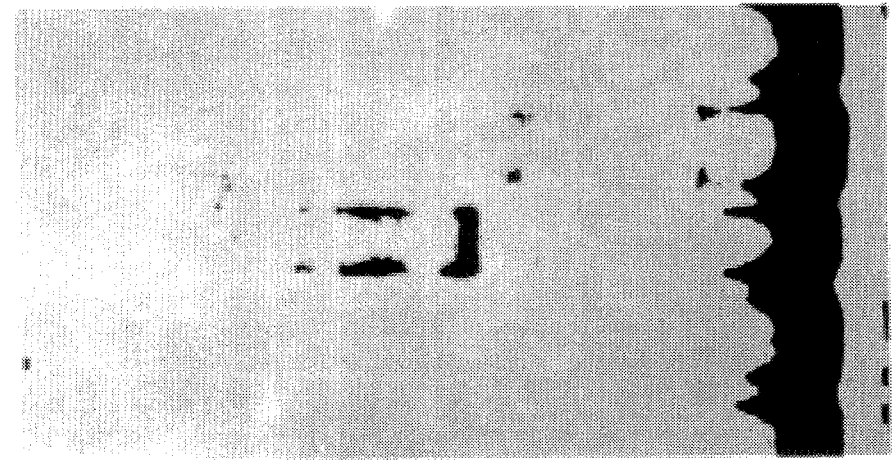

Two cDNAS were isolated by this method (FIG. 13). These were termed ILF-1 (FIG. 14; SEQUENCE ID NO: 1) and ILF-2 (FIG. 15; SEQUENCE ID NO: 3). The predicted amino acid sequences of ILF-1 and ILF-2 are also shown in each of these figures and are represented by SEQ ID NO:2 and SEQ ID NO:33, respectively.

Figure 10A:
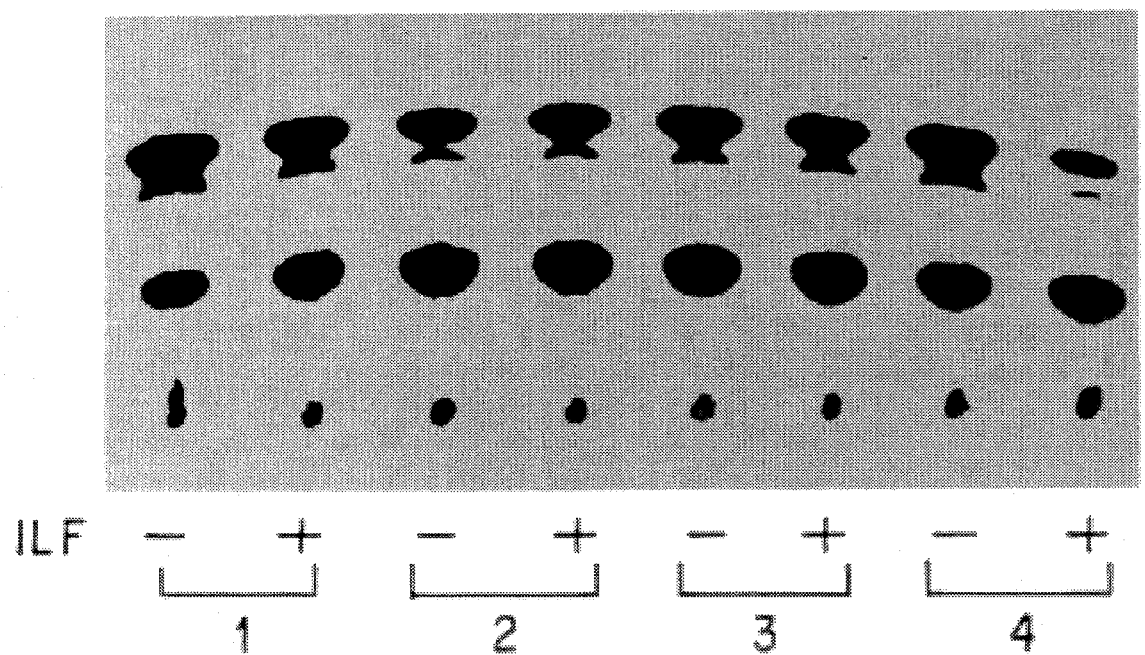
FIG. 10. ILF represses full length but not truncated IL-2 CAT constructs. (A) A chromatogram showing CAT gene expression in extracts prepared from transfected Jurkat cells stimulated with TPA, PHA, and ionomycin. IL-2 promoter fragments extending from either –72, –240, –273 or –342 to +47 were placed upstream to the CAT reporter gene. 10 μg of each IL-2 CAT reporter construct was co-transfected into Jurkat cells by electroporation with 10 μg of a eukaryotic expression construct containing either the β-globin gene (–ILF) or the ILF cDNA (+ILF). At 28 hours post transfection, cells were harvested, extracts prepared and CAT activity determined. The ratio of $^{14}$C chloramphenicol conversion in the absence and presence of ILF is (1) 0.92, (2) 1.0, (3) 1.0, (4) 0.17. (B) A schematic representation of the IL-2 promoter constructs fused to the CAT gene with previously characterized binding sites (for NFAT, NFkB and CD28) and the transcriptional start site in the IL-2 gene indicated.
Figures 1, 10B:
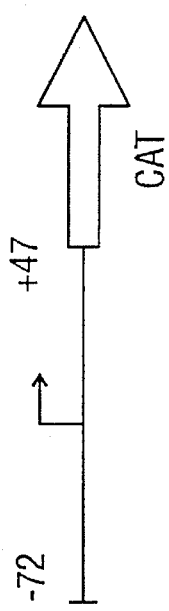
FIG. 1. Production of β-galactosidase fusion proteins from λgt11 isolates. Lysates were prepared from E. coli infected with either λgt11 (lanes 1 and 2), or from a λgt11 isolate containing a portion of the ILF cDNA (lanes 3 and 4). β-galactosidase (lane 3) and the β-galactosidase/ILF fusion (lane 4) were purified using anti-β-galactosidase sepharose chromatography. The samples were electrophoresed on 10% SDS-polyacrylamide gels and Coomassie stained (A). Western blot analysis of affinity purified samples was performed with antibody directed against either β-galactosidase (B) or ILF (C). The molecular weights of the marker proteins are given on the left. Lane 1, β-galactosidase; lane 2, β-galactosidase-ILF fusion protein; lane M, molecular weight markers.
Figures 2, 10B:
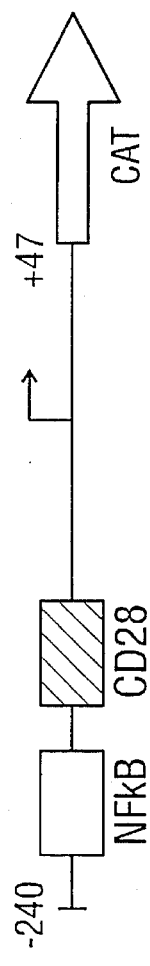
Figures 3, 10B:
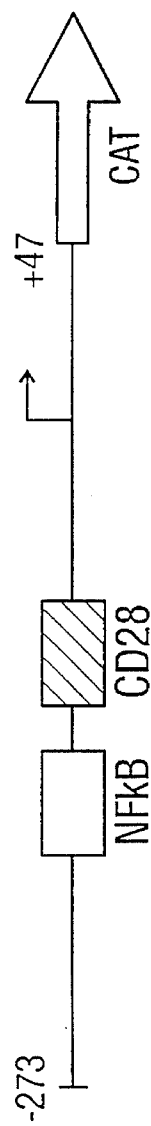
Figures 4, 10B:
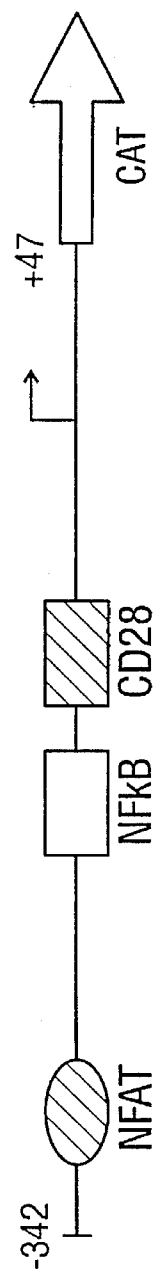
FIG. 4. Homology of the ILF DNA binding domain. The amino acid sequence of a portion of the ILF DNA binding domain (amino acids 138 −236) is aligned with the DNA binding domains of the Drosophila fork head protein (208–306) and the hepatocyte factor HNF-3A (168–266). ("x") indicates amino acid identity and ("·") indicates conservative amino acid changes.

The sequence analysis revealed that both clones were identical except in their carboxyl-termini (FIGS. 1–3). Both cDNAs had an identical initiating methionine with a stop codon noted 138 bp upstream. In addition, both clones contained potential fork head DNA binding domains. However, in their carboxyl-termini, ILF-1 maintains an open reading frame until nucleotide 2147, while ILF-2 contains an additional 422 nucleotides inserted between positions 1953 and 2374, resulting in a protein that differs by 65 amino acids from the carboxyl terminus of ILF-1.

EXAMPLE 5

CHARACTERIZATION OF ILF IN DIFFERENT CELL LINES AND TISSUE TYPES

The present example is provided to demonstrate the utility of the present invention for use in a wide range of cell lines and tissue types. The data presented establishes that the newly characterized ILF protein and the uses described herein therefore are not limited to the particular in vitro or in vivo exemplary cell lines and animal models examined, but have application also in human systems. In addition, the present example demonstrates the utility for examining particular pathologic conditions, such as the neoplastic lymphomas, in relation to the role of ILF and ILF gens expression in those and related diseases.

Using the PCR technique, the present inventors have established that ILF is expressed in a number of cell lines and tissue types. These cell lines and tissue types are listed in Table 2.

TABLE 2

| Cell Lines and Tissue Types and ILF Gene Expression | |
|---|---|
| Cell Lines | ILF Expression |
| Jurkat lymphocytes | + |
| HUT 78 lymphocytes | + |
| Hela cells | + |
| U937 cells | + |
| HepG$_2$ cells | + |
| HL60 granulocytes | + |

In addition, it has been found that ILF mRNA transcripts are alternatively processed in a tissue specific manner. In this regard, lymphoid-specific forms of ILF have been characterized which delete the fork head DNA binding domain of ILF. The function of these truncated proteins remains to be determined.

ILF Expression in Pathological Specimens

The present studies are also directed to determining the functional significance of alternatively processed mRNAs in pathological specimens, particularly neoplastic lymphoid or myeloid tissue. The mapping of the ILF gens to human chromosome 17q25 is interesting. This region is deleted in a variety of acute leukemias and lymphomas. Studies are underway to determine if ILF is rearranged in human leukemias. Chromosomal mapping, Northern, Southern, and PCR analysis of RNA and DNA from leucitic cells will be performed to analyze changes in the ILF gene. DNA probes for the ILF gene will be used to analyze abnormal expression in lymphomas and leukemias.

EXAMPLE 6

CHROMOSOMAL MAPPING OF THE ILF GENE

The present example is provided to demonstrate the determination of the chromosomal position of the ILF gene. Such studies may prove valuable in the molecular analysis of possible translocations affecting this gene.

Chromosomal mapping. A panel of 17 mouse-human somatic cell hybrid clones was constructed and analyzed for chromosome content as described by Mohandas et al., (1986). DNA was isolated from nuclei of these clones as well as from the parental mouse cell line (B82GM 0347A) and human lymphocytes using sodium dodecyl sulfate (SDS) and proteinase K followed by phenol-chloroform extraction. Following cleavage with restriction enzymes, 10 µg of the DNA from each sample was electrophoresed through a 1.2% agarose gel and transferred by blotting to a nylon filter (Mehrabian et al., 1986). The filters were then probed with the ILF cDNA. After isolation by preparative gel electrophoresis, the insert was radiolabeled with [$^{32}$P] dCTP by a random priming method (Feinberg and Vogelstein, 1983) to a specific activity of about 1×10$^9$ cpm/mg (Mehrabian et al., 1986). Filter hybridization and autoradiography were performed according to Mehrabian et al., (1986).

For in situ hybridization, the ILF cDNA insert was labeled by random priming with $^3$H-labeled deoxynucleotides to a specific activity of about 4×10$^8$ cpm/mg. The probe was then hybridized to chromosomes from normal human lymphocytes using the method of Harper and Saunders (1981) as modified by Cannizzaro and Emanuel (1984). The slides were exposed for 10 days, and silver grains on or touching chromosomes were scored.

Figure 17:
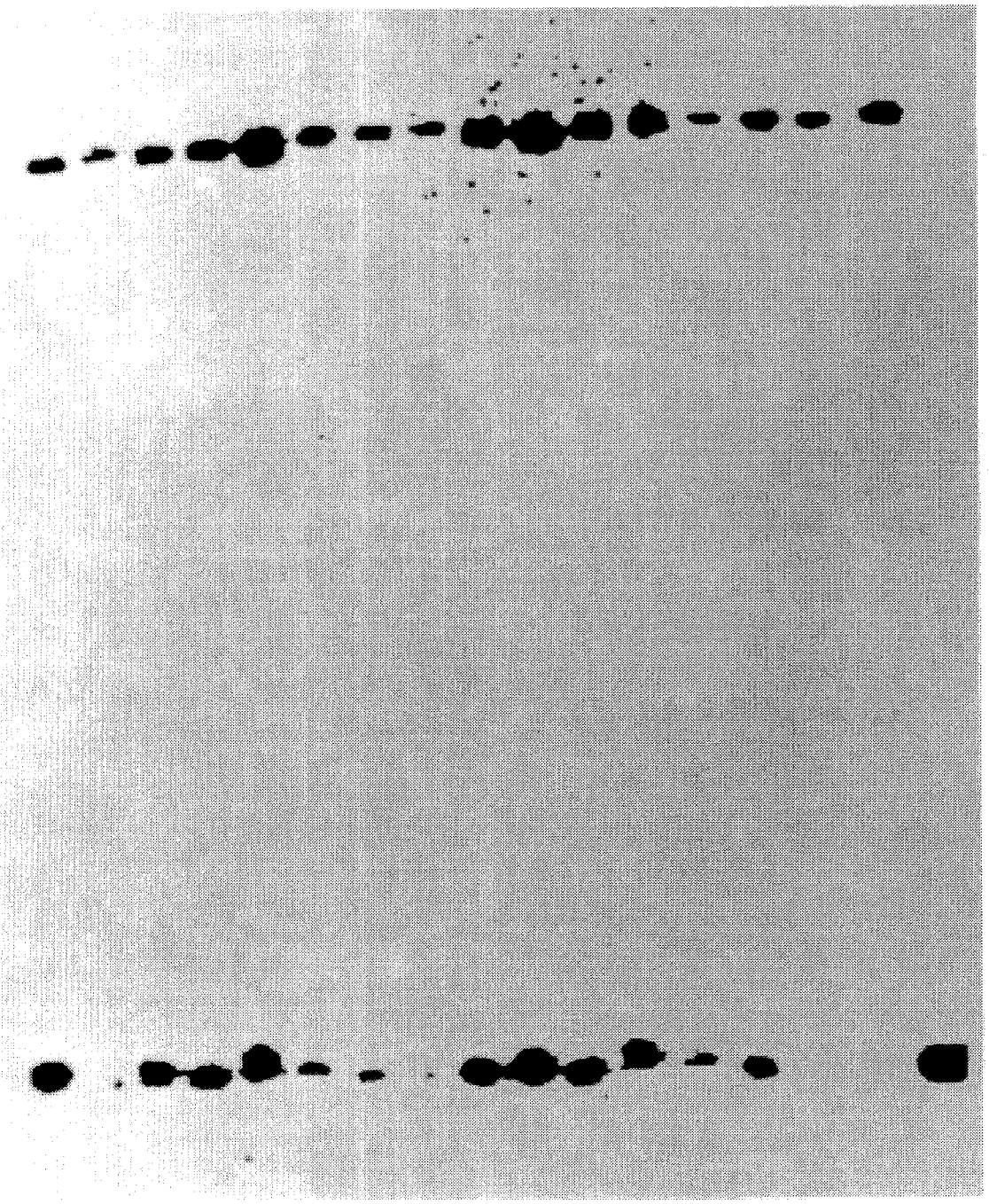
FIG. 17. Southern analysis of mouse-human somatic cell hybrids with ILF. DNA was isolated from a variety of previously described somatic cell hybrids including 84-24, 7, 20, 21, 25, 26, 27, 30, 34, 35, 37, 38, 39, and 116-5 (lanes 1–15), a parental mouse cell line (lane 16), and a human cell line (lane 17), followed by digestion with HindIII. An ILF fragment was labeled by random priming and used in Southern analysis. The position of the 2.0-kb HindIII fragment in human DNA is indicated.

The chromosomal localization of the ILF gene was determined by Southern blotting analysis of a panel of mouse-human genetic cell hybrids derived by fusion of normal male fibroblasts (IMR 91) with thymidine kinase-deficient mouse B82 cells (Mohandas et al., 1986). The hybrids contained varying complements of human chromosomes as determined by karyotyping, and they have now been used for the chromosomal assignment of a large number of human genes. After digestion of genomic DNA prepared from the hybrid cell lines with HindIII, two major bands of 17 and 2.0 kb were noted upon blotting analysis with ILF cDNA (FIG. 17, lanes 1–14). Mouse genomic DNA alone yielded a hybridizing band of about 17 kb (FIG. 17, lane 16), while human DNA yielded only the 2.0-kb hybridizing band (FIG. 17, lane 17).

Blotting analysis of HindIII-digested DNA form the panel of 15 mouse-human somatic cell hybrids revealed that the 2.0-kb human band cosegregated with chromosome 17, and all clones except 116-5 exhibited this band (FIG. 17, lane 15). Thus all the clones except 116-5 contained chromosome 17 (FIG. 17). Multiple discordancies were observed between the segregation pattern of the human ILF gene and all other chromosomes.

Figure 18:
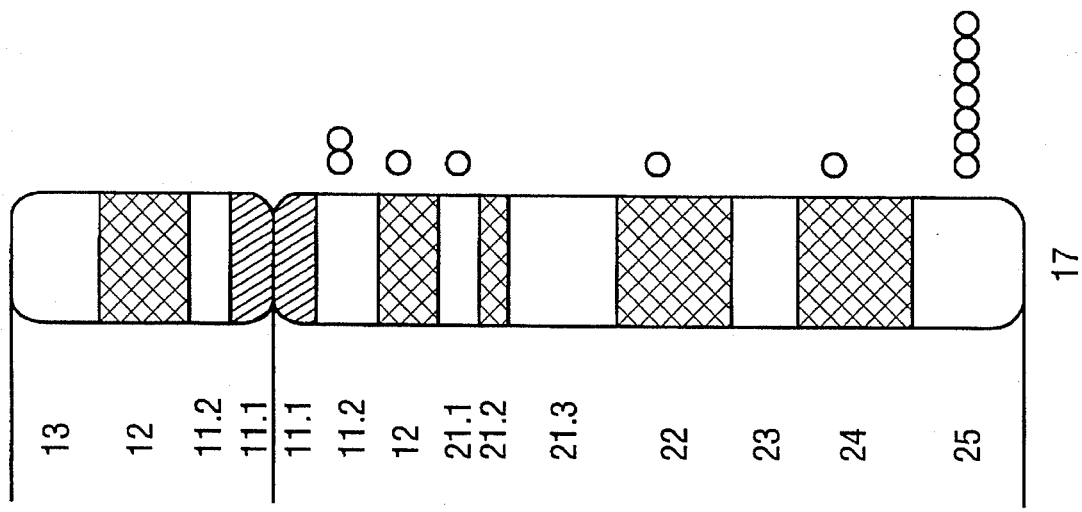
FIG. 18. Chromosomal localization of ILF by in situ hybridization. Metaphase chromosomes from normal human lymphocytes were hybridized with an ILF fragment labeled by random priming. The slides were exposed for 1 week and developed, and the grains touching chromosomes were scored. In an examination of 45 cells, the peak grain concentration occurred on chromosome 17, although a high background was noted. Of a total of 41 grains scored, 13 were on the long arm of chromosome 17 and 7 were on 17q25.

The regional localization of the ILF gene was examined by in situ hybridization to normal metaphase chromosomes. A significant accumulation of genes was observed only on the short arm of chromosome 17 with peak accumulation in the 17q25 region (FIG. 18). These results confirm the somatic cell hybrid analysis studies and further localize the ILF gene to human chromosome 17q25.

The localization of ILF to chromosome 17q25 is interesting. This region is the localization site of genes for a homologue of the v-erb-A oncogene, procollagen, 2-oxoglutarate 4-dioxygenase, and protein disulfide isomerase (Solomon & Baker, 1989). In addition, the long arm of chromosome 17 is the site of translocations in human acute myelogenous leukemia. In particular, translocations of chromosome 11 and 17 t(11/17)(q23D5) have been noted (Bloomfield & de la Chapelle, 1987). Interestingly a number of these translocations involve the displacement of ets-1 oncogene, which is located on 11q23 (Watson et al., 1988). Since the Ets1 protein can bind to NFAT motifs, it is interesting to speculate whether this translocation could potentially involve the substitution of the Ets1 and ILF binding domains. Studies of clinical leukemia specimens will determine whether the ILF is the site of potential translocations in human leukemia involved in this translocation.

PROPHETIC EXAMPLE 7 PROPOSED METHOD FOR TREATING HIV-RELATED INFECTION WITH ILF INHIBITORS

The present example is provided to demonstrate a most preferred method whereby the ILF protein factor and/or the gene encoding the ILF protein factor may be used to treat an HIV-infection in an animal.

ILF Protein

Where the agent to be used as the therapeutic agent is the nucleic acid binding factor peptide corresponding to the ILF fork head domain (such as a peptide having an amino acid sequence corresponding to SEQ ID NO: 2 or SEQ ID NO: 33), the ILF (ILF-1 or ILF-2) will be suspended in a pharmacologically acceptable diluent which is suitable for injection into an animal. By way of example, such a diluent would be sterile saline. Where the treatment is being prepared for injection to a human, the most preferred concentration of ILF/ml of diluent would be about 100 mg/l. The amount of the ILF to be administered is to be calculated based on the weight of the patient. In this regard, and by way of example, where the patient weighs about 70 kg, the ILF should be administered at a dose of about 10 mg/kg, a total dose of about 700 mg for a 70 kg patient would be therefore be administered daily in a volume about 7 ml of the 100 mg/ml preparation described above.

Daily treatments with the ILF would be discontinued upon the observation of a sustained general improvement in the overall conditions of the patient. By way of example, such improvements may include patient weight gain or an observable decrease in observable HIV virus in a patients blood or other biological fluid sample, and an increase in the blood level of $CD_4^+$ lymphocytes. The recombinant ILF protein may alternatively be formulated as a tablet according to tableting protocols generally known to those of skill in the art (Remingtons Pharmaceutical Sciences, 18th edition (1990) Alfonso R. Gennaro, editor Mack Publishing Company Easton, Pennsylvania) which reference is specifically incorporated herein in pertinent part for this purpose.

ILF Gene

Where the agent to be used as a therapeutic agent includes the IlF gene, it is contemplated that the ILF gene will be incorporated into a vector sequence. By way of example, the ILF gene sequence to be employed is a nucleotide sequence corresponding substantially to the ILF-1 or ILF-2 nucleotide sequence provided in SEQUENCE ID NO: 1 or SEQUENCE ID NO: 3, respectively. This recombinant vector may then be used to treat the animal as a whole, or may be directed to specific cell types injected with the HIV virus. In order to direct the vector to HIV-infected all types specifically, the vector may be coupled with an antibody which is specific for any of a number of HIV-infected all surface antigens. Such HIV-cell surface antigens include, by way of example, gp120, and gp160 or IL-2.

The recombinant vector will be formulated so as to be suitable as a liquid injectable solution physiologically compatible for injection into a human patient. The particular recombinant vector may take the form of the recombinant vector described herein. The ILF gene, either in part or complete, could be expressed in retroviral expression vectors which are used to infect human cells to inhibit HIV gene expression. Furthermore, inhibitors of ILF gene expression or splicing may be useful to inhibit HIV-1 gene expression.

In addition, the ILF gene or peptides can be used to inhibit patients lymphocytes which are activated due to rheumatic or other autoimmune mechanisms. Thus, either peptides corresponding to the ILF DNA binding domain or portions of the ILF protein may be useful to inhibit IL-2 gene expression in patients.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary, procedural or other details supplementary to those set forth herein, are specifically incorporated herein by reference.

Ausbabel, F. M., Brent, R., Kingston, R. E., Moore, D. E., Smith, J. A., Seidman, J. G., and Struhl, K. (1987). *Current Protocols in Molecular Biology,* eds. John Wiley and Sons.

Baichwal, V. R. and Tjian, R. (1990). *Cell* 63:815.

Bloomfield, C. D., and de la Chapelle, A. (1987). *Semin. Onc.* 14:372–383.

Burglin, T. R. and De Robertis, E. M. (1987). *EMBO J.* 6:2617–2625.

Cannizzaro, C. A., and Emanuel, B. S. (1984). *Cytogenet. Cell Genet.* 38:308–309.

Capaldi et al. *Biochem. Biophys. Res. Comm.* 76:425 (1977).

Chatila, T., Castigli, E., Pahwa, R., Pahwa, S., Chirmile, N., Oyaiza, N., Good, R. A., and Geha, R. S. (1990) *PNAS USA.* 87:10033–10037.

Costa, R. H., Grayson, D. R., and Darnell, J. E. (1989). *Mol. Cell. Biol.* 9:1415–1425.

Crabtree, G. R. (1989). *Science* 243:355–361.

Emmel E. A., Verweij C. L., Durand D. B., Higgins K. M., Lacy E., Crabtree G. R. (1989). *Science* 246:1617–1620.

Feinberg, A., and Vogelstein, B. (1983). *Anal. Biochem.* 132:6–13.

Flanagan, J. R. et al. (1991b) *Proc. Natl. Acad. Sci. USA* 88:3145

Flanagan, W. M., Corthesy, B., Bram, R. J., and Crabtree, G. R. (1991a) *Nature* 352:803.

Fujita, T., Shibuya, H., Ohashi, T., Yamanishi, K., and Taniguchi, T. (1986). *Cell* 46:401–407.

Garcia, J. A., Harrich, D., Soultanakis, E., Wu, F., Mitsuyasu, R., and Gaynor, R. B. (1989). *EMBO J.* 8:765–778.

Gaynor, R. B., Kuwabara, M. D., Wu, F. K., Garcia, J. A., Harrich, D., Briskin, M., Wall, R., and Sigman, D. S. (1988) *Proc. Natl. Acad. Sci. USA* 85:9406–9410.

Glotzer, M., Murray, A. W., and Kirschner, M. W. (1991). *Nature* 349:132–138.

Gorman, C. M., Moffet, L. F., and Howard, B. H. (1982) *Mol. Cell. Bio.* 2:1044.

Harper, M. E., and Saunders, G. S. (1981). *Chromosoma* 83:431–439.

Karim, F. D., Urness, L. D., Thummel, C. S., Klemsz, M. J., McKercher, S. R., Celada, A., Van Beveren, C., Maki, R. A., Gunther, C. V., Nye, J. A., and Graves, B. J. (1990). *Genes & Dev.* 4: 1451–1453

Klemsz, M. J., McKercher, S. R., Celada, A., Van Beveren, C., and Maki, R. A. (1990). *Cell* 61:113–124.

Kozak, M. (1983) *Microbiol. Rev.* 47:1–45.

Lai, E., Prezioso, V. R., Smith E., Litvin, O., Costa, R. H., and Darnell, J. E. (1990). *Genes & Dev.* 4:1427–1436.

Lai, E. Prezioso, V. R., Tao, W., Chen, W. S., and Darnell, J. E. (1991). *Genes & Dev.,* 5:416–427.

Lu, Y., Touzjian, N., Stenzel, M., Dorfman, T., Sodroski, J. G., and Haseltine, W. A. (1990). *J. Virol.* 64:5226–5229.

Madden S. L. et al. (1991) *Science* 253:1550.

Mehrabian, M., Sparkes, R. S., Mohandas, T., Klisak, I. J., Schumaker, V. N., Heinzman, C., Zollman, S., Ma, Y., and Lusis, A. J. (1986). *Somt. Cell Mol. Genet.* 12:245–254.

Mohandas, T., Heinzmann, C., Sparkes, R. S., Wasmuth, J., Edwards, P., and Lusis, A. J. (1986). *Somt. Cell Mol. Genet.* 12:89–94.

Montminy, M. R., Sevarino, K. A., Wagner, J. A., Mandel, G., and Goodman, R. H. (1986) *Proc. Natl. Acad Sci USA* 86:4887–4891.

Muchardt, C., Li, C., Kornuc, M., and Gaynor, R. (1990). *J. Virol.* 64: 4296–4305.

Nabel, G. and Baltimore, D. (1987). *Nature* 326:711–713.

Novak, T. J., Chen, D., and Rothenberg, E. V. (1990). *Mol. Cell. Biol.* 10:6325–6334.

Pettersson, M., and Schaffner, W. (1987). *Genes Dev.* 1:962–972.

Randak, C., Brabletz, T., Hergenrother, M. Sobotta, I., and Serfling, E. (1990). *EMBO J.* 9:2529–2536.

Remington Pharmaceutical Sciences, 18th edition, (1990) Alfonso R. Gerraro, editor, Mack Publishing Co., Easton, Pa.

Rosen C. A., Sodroski, J. G., Haseltine, W. A. (1985) *Cell* 41:813–823.

Shaw, J. P., Utz, P. J., Durand, D. B., Toole, J. J., Emmel, E. A., and Crabtree, G. R. (1988). *Science* 241:202–205.

Siekevitz, M., Josephs, S. F., Dukovich, M., Peffer, N., Wong-Staal, F., and Greene, W. C. (1987) *Science* 238:1575–1578.

Siekevitz, M., Josephs, S. F., Dukovich, M., Peffer, N., Wong-Staal, F., and Greene, W. C. (1987) *Science* 238:1575–1578.

Singh H., LeBowitz J. H., Baldwin Jr. L. S., and Sharp P. A. (1988). *Cell* 52:4155–4163.

Smith, D. B., and Johnson, K. S. (1988). *Gene* 67:31–37.

Solomon, E., and Baker, D. F. (1989). *Cytogenet. Cell Genet.* 51:319–337.

Tong-Starksen S. E., Luciw P. A., and Peterlin B. M. (1987). *Proc. Natl. Acad. Sci. USA* 84:6845–6849.

Watson, D. K. McWilliams-Smith, M. J., Nunn, M. F. Duesberg, P. H., O'Brian, J., and Papas, T. S. (1988). *Proc. Natl. Acad. Sci. USA* 85:7862–7866.

Weigel, D., and Jackle, H. (1990). *Cell* 63:455–456.

Weigel, D., Jurgens, G., Kuttner, F., Seifert, E., and Jackle, H. (1989). *Cell* 57:645–658.

Wierenga, R. K., and Hol, W. G. J. (1983). *Nature* 302:842–844.

What is claimed is:

1. A DNA molecule encoding a nucleic acid binding factor protein characterized by the following properties:
   binding with a NFAT-like DNA motif altering HIV gene expression; and containing a fork head DNA binding domain, said nucleic acid binding factor protein having a molecular weight of about 60kDa as determined by sucrose gradient.

2. The DNA molecule of claim 1 comprising the nucleic acid sequence set forth in SEQ ID NO:1 or SEQ ID NO:3.

3. The DNA molecule of claim 1, further defined as encoding a binding protein comprising an amino acid sequence set forth in SEQ ID NO:2 or SEQ ID NO:33.

4. A recombinant vector comprising a DNA molecule in accordance with claim 1 or 2, wherein the nucleic acid binding factor regulates the expression of an interleukin-2 gene in T-lymphocytes.

5. A recombinant host cell comprising a recombinant DNA molecule corresponding to the DNA molecules of claim 1 or 2.

6. The recombinant host cell of claim 5 wherein the recombinant DNA molecule includes a recombinant vector sequence.

7. The recombinant host cell of claim 5, further defined as a eukaryotic host cell.

8. The recombinant host cell of claim 5, further defined as a bacterial host cell.

9. The recombinant host cell of claim 5, wherein the DNA molecule is integrated into the genome of the host cell.

10. A recombinant host cell having a DNA molecule in a recombinant vector, wherein the DNA molecule comprises the nucleic acid sequence of SEQ ID NO:1 or SEQ ID NO:3.

11. The recombinant host cell of claim 10 wherein the recombinant vector is pGEX or Pdp18.

* * * * *

UNITED STATES PATENT AND TRADEMARK OFFICE
CERTIFICATE OF CORRECTION

PATENT NO.    :   5,534,631

DATED         :   July 9, 1996

INVENTOR(S)   :   Ching Li, Richard b. Gaynor and Ajay Nirula

It is certified that error appears in the above-identified patent and that said Letters Patent is hereby corrected as shown below:

Title page, item [57], line 19, please delete "gene expression maxially when" and insert -- gene expression maximally when -- therefor.

Signed and Sealed this

Twenty-sixth Day of May, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 2517 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:1:

```
GTATTCGTGG ACGGCGTGTT CCAGAGGCGC GGGGCGCCGC CGCTGCAGCT GCCGCGCGTG      60
TGCACATTCA GGTTCCCGAG CACAAACATC AAGATAACGT TCACTGCCCT GTCCAGCGAG     120
AAGAGAGAGA AGCAGGAGGC GTCTGAGTCT CCAGTGAAGG CCGTACAGCC ACACATCTCG     180
CCCCTGACCA TCAACATTCC AGACACCATG GCCCACCTCA TCAGCCCTCT GCCCTCCCCC     240
ACGGGAACCA TCAGCGCTGC AAACTCCTGC CCTCCAGCC CCCGGGGAGC GGGGTCTTCA      300
GGGTACAAGG TGGGCCGAGT GATGCCATCT GACCTCAATT TAATGGCTGA CAACTCACAG     360
CCTGAAAATG AAAGGAAGC TTCAGGTGGA GACAGCCCGA AGGATGATTC AAAGCCGCCT      420
TACTCCTACG CGCAGCTGAT AGTTCAGGCG ATTACGATGG CTCCCGACAA ACAGCTCACC     480
CTGAACGGGA TTTATACACA CATCACTAAA AATTATCCCT ACTACAGGAC TGCGGACAAG     540
GGCTGGCAGA ATTCAATTCG CCACAATCTC TCTCTGAATC GTTATTTCAT CAAAGTGCCG     600
CGTTCCCAGG AAGAACCAGG CAAAGGCTCG TTCTGGAGGA TAGACCCAGC CTCTGAAAGC     660
AAATTAATAG AACAGGCTTT TAGGAAACGA CGGCCTAGGG GCGTGCCCTG CTTTAGAACC     720
CCTCTGGGAC CGCTCTCTTC TAGGAGTGCC CCAGCCTCTC CCAATCACGC GGGAGTGCTG     780
TCTGCTCACT CTAGTGGCGC CCAGACCCCT GAGAGCCTGT CGAGGGAAGG TTCGCCGGCC     840
CCCCTGGAGC CTGAGCCTGG CGCTGCACAG CCCAAACTCG CTGTCATCCA GGAAGCCCGG     900
TTTGCCCAGA GCGCCCCAGG GTCACCTCTG TCCAGTCAGC CAGTCTTAAT CACCGTCCAG     960
CGGCAGCTAC CACAGGCCAT CAAGCCTGTC ACCTACACTG TGGCCACCCC AGTGACCACC    1020
TCGACCTCCC AGCCACCCGT CGTGCAGACG GTTCACGTCG TCCACCAGAT CCCAGCGGTG    1080
TCGGTCACCA GTGTGGCCGG ACTGGCCCCA GCGAACACGT ACACTGTCTC TGGACAAGCT    1140
GTGGTCACCC CGGCAGCCGT GCTGGCCCCT CCTAAGGCAG AGGCCCAGGA GAATGGAGAC    1200
CACAGGGAAG TCAAAGTGAA AGTAGAGCCT ATTCCCGCCA TTGGCCACGC CACGCTCGGC    1260
ACTGCCAGCC GGATCATTCA GACGGCACAG ACCACCCCGG TCCAGACGGT GACCATAGTA    1320
CAACAGGCAC CTCTAGGTCA ACACCAGCTA CCAATAAAAA CTGTAACACA AACGGCACT    1380
CACGTGGCAT CAGTCCCCAC TGCGGTCCAC GGCCAGGTGA ACAATGCCGC GGCGAGTCCT    1440
TTGCACATGT TGGCAACACA CGCATCCGCA TCGGCCTCCC TGCCCACAAA GCGCCACAAC    1500
GGTGACCAGC CGGAGCAGCC GGAGCTGAAG CGGATCAAGA CAGAAGACGG CGAGGGCATC    1560
GTCATTGCCC TGAGCGTGGA CACGCCACCG GCAGCCGTAA GGGAAAAGGG TGTCCAGAAC    1620
TAGCGACCGG GAGAGCTTTT CTTTAACGAT ATCAACTCTG TGGTGCCAAA AGGAGACGCG    1680
GCCTCCCGCC AGCACTCGGG GGTGCAGGGC CTGTGGTTG GACTTCACCT CTCAGCACTG     1740
AAAACCCAAA ACCCAGCTGG CCTTAACACT CCTTAAAGAC AGAAGTCACA CTTGAACAAA    1800
ACCCACACAC AACAAAACCT GATTTGGGAG ACGGTGTCTC CACTGAGCAC CTGCTGGGCT    1860
GAGCTTCTAC CTACGAGTGA AACTCTGTCC TCCCGCGAGG ACCAGGCATC GCTGTGTGAG    1920
GACGGCACGG CCAGCGCCTG CTGTGAGTGG GTCTCCCAAG ACTAGGCCTC AGGACGCGGG    1980
```

```
GGGAGCCATC  CCCGCCGCCC  TCACAGGACC  CACCAGGCAG  CGGAGACATG  TGGAATTAGA      2040

GTATTTTGAG  GTGTCCTTTC  TTTACAAAAT  AATGGGGTCT  TGGGCATTTC  ACATCACTCC      2100

ATTTCTACTG  AGACTTTCAG  AATCACACAG  GCCCTTTCCG  TGGATTTCAT  TTGGGGCAAA      2160

GAAACAACAT  AGTTTTGTTT  TTGTTTTCAG  CCTATGGAAT  GATTCCTTT   TGTCTGTCTT      2220

GTTCAAGTTC  AGACGAAGCT  ACTCTGGCAT  CTGCACATTT  CCGTGTTACA  GCAGCTGCCT      2280

GATGAATTTT  ATCCACCTCC  ATTTCAGCAT  GTGGCTCGCG  TGGACAGGTG  GACGGACGCT      2340

GTGGCCGCAT  GGAACCTTGA  GAACCCAGGG  ACGAGCCAGT  GCCGGGAAGG  AACTGCCGGG      2400

ACTCACCGAG  CTGCACTTAA  CTGTTCTCTT  TCTGGCTATT  TTTGTTGTT   TGTTTCTTTG      2460

TGTTGACTTT  GTCCCTGGCA  AAATTTTCCA  CTCTGAGTAA  AACAAGTCTC  GGAATTC         2517
```

(2) INFORMATION FOR SEQ ID NO:2:

(i) SEQUENCE CHARACTERISTICS:
        (A) LENGTH: 540 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Val  Phe  Val  Asp  Gly  Val  Phe  Gln  Arg  Arg  Gly  Ala  Pro  Pro  Leu  Gln
 1              5                        10                       15

Leu  Pro  Arg  Val  Cys  Thr  Phe  Arg  Phe  Pro  Ser  Thr  Asn  Ile  Lys  Ile
                20                       25                       30

Thr  Phe  Thr  Ala  Leu  Ser  Ser  Glu  Lys  Arg  Glu  Lys  Gln  Glu  Ala  Ser
           35                        40                       45

Glu  Ser  Pro  Val  Lys  Ala  Val  Gln  Pro  His  Ile  Ser  Pro  Leu  Thr  Ile
     50                       55                       60

Asn  Ile  Pro  Asp  Thr  Met  Ala  His  Leu  Ile  Ser  Pro  Leu  Pro  Ser  Pro
 65                      70                       75                       80

Thr  Gly  Thr  Ile  Ser  Ala  Ala  Asn  Ser  Cys  Pro  Ser  Ser  Pro  Arg  Gly
                85                       90                       95

Ala  Gly  Ser  Ser  Gly  Tyr  Lys  Val  Gly  Arg  Val  Met  Pro  Ser  Asp  Leu
               100                      105                      110

Asn  Leu  Met  Ala  Asp  Asn  Ser  Gln  Pro  Glu  Asn  Glu  Lys  Glu  Ala  Ser
          115                       120                      125

Gly  Gly  Asp  Ser  Pro  Lys  Asp  Asp  Ser  Lys  Pro  Pro  Tyr  Ser  Tyr  Ala
     130                      135                      140

Gln  Leu  Ile  Val  Gln  Ala  Ile  Thr  Met  Ala  Pro  Asp  Lys  Gln  Leu  Thr
145                      150                      155                      160

Leu  Asn  Gly  Ile  Tyr  Thr  His  Ile  Thr  Lys  Asn  Tyr  Pro  Tyr  Tyr  Arg
               165                      170                      175

Thr  Ala  Asp  Lys  Gly  Trp  Gln  Asn  Ser  Ile  Arg  His  Asn  Leu  Ser  Leu
               180                      185                      190

Asn  Arg  Tyr  Phe  Ile  Lys  Val  Pro  Arg  Ser  Gln  Glu  Glu  Pro  Gly  Lys
          195                      200                      205

Gly  Ser  Phe  Trp  Arg  Ile  Asp  Pro  Ala  Ser  Glu  Ser  Lys  Leu  Ile  Glu
     210                      215                      220

Gln  Ala  Phe  Arg  Lys  Arg  Arg  Pro  Arg  Gly  Val  Pro  Cys  Phe  Arg  Thr
225                      230                      235                      240

Pro  Leu  Gly  Pro  Leu  Ser  Ser  Arg  Ser  Ala  Pro  Ala  Ser  Pro  Asn  His
               245                      250                      255
```

| | | | | | | | | | | | | | | |
|---|---|---|---|---|---|---|---|---|---|---|---|---|---|---|
|Ala|Gly|Val|Leu<br>260|Ser|Ala|His|Ser|Ser<br>265|Gly|Ala|Gln|Thr|Pro<br>270|Glu|Ser|
|Leu|Ser|Arg<br>275|Glu|Gly|Ser|Pro|Ala<br>280|Pro|Leu|Glu|Pro<br>285|Glu|Pro|Gly|Ala|
|Ala|Gln|Pro<br>290|Lys|Leu|Ala|Val|Ile<br>295|Gln|Glu|Ala|Arg<br>300|Phe|Ala|Gln|Ser|
|Ala<br>305|Pro|Gly|Ser|Pro|Leu<br>310|Ser|Ser|Gln|Pro|Val<br>315|Leu|Ile|Thr|Val|Gln<br>320|
|Arg|Gln|Leu|Pro|Gln<br>325|Ala|Ile|Lys|Pro|Val<br>330|Thr|Tyr|Thr|Val|Ala<br>335|Thr|
|Pro|Val|Thr|Thr<br>340|Ser|Thr|Ser|Gln|Pro<br>345|Pro|Val|Val|Gln|Thr<br>350|Val|His|
|Val|Val|His<br>355|Gln|Ile|Pro|Ala|Val<br>360|Ser|Val|Thr|Ser|Val<br>365|Ala|Gly|Leu|
|Ala|Pro<br>370|Ala|Asn|Thr|Tyr|Thr<br>375|Val|Ser|Gly|Gln|Ala<br>380|Val|Val|Thr|Pro|
|Ala<br>385|Ala|Val|Leu|Ala|Pro<br>390|Pro|Lys|Ala|Glu|Ala<br>395|Gln|Glu|Asn|Gly|Asp<br>400|
|His|Arg|Glu|Val|Lys<br>405|Val|Lys|Val|Glu|Pro<br>410|Ile|Pro|Ala|Ile|Gly<br>415|His|
|Ala|Thr|Leu|Gly<br>420|Thr|Ala|Ser|Arg|Ile<br>425|Ile|Gln|Thr|Ala|Gln<br>430|Thr|Thr|
|Pro|Val|Gln|Thr<br>435|Val|Thr|Ile|Val<br>440|Gln|Gln|Ala|Pro|Leu<br>445|Gly|Gln|His|
|Gln|Leu|Pro<br>450|Ile|Lys|Thr|Val<br>455|Thr|Gln|Asn|Gly|Thr<br>460|His|Val|Ala|Ser|
|Val<br>465|Pro|Thr|Ala|Val|His<br>470|Gly|Gln|Val|Asn|Asn<br>475|Ala|Ala|Ala|Ser|Pro<br>480|
|Leu|His|Met|Leu|Ala<br>485|Thr|His|Ala|Ser|Ala<br>490|Ser|Ala|Ser|Leu|Pro<br>495|Thr|
|Lys|Arg|His|Asn<br>500|Gly|Asp|Gln|Pro|Glu<br>505|Gln|Pro|Glu|Leu|Lys<br>510|Arg|Ile|
|Lys|Thr|Glu<br>515|Asp|Gly|Glu|Gly|Ile<br>520|Val|Ile|Ala|Leu|Ser<br>525|Val|Asp|Thr|
|Pro|Pro<br>530|Ala|Ala|Val|Arg|Glu<br>535|Lys|Gly|Val|Gln|Asn<br>540| | | | |

(2) INFORMATION FOR SEQ ID NO:3:

(i) SEQUENCE CHARACTERISTICS:
        (A) LENGTH: 2939 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="DNA"

(xi) SEQUENCE DESCRIPTION: SEQ ID NO:3:

| | | | | | |
|---|---|---|---|---|---|
|GTATTCGTGG|ACGGCGTGTT|CCAGAGGCGC|GGGGCGCCGC|CGCTGCAGCT|GCCGCGCGTG|60|
|TGCACATTCA|GGTTCCCGAG|CACAAACATC|AAGATAACGT|TCACTGCCCT|GTCCAGCGAG|120|
|AAGAGAGAGA|AGCAGGAGGC|GTCTGAGTCT|CCAGTGAAGG|CCGTACAGCC|ACACATCTCG|180|
|CCCCTGACCA|TCAACATTCC|AGACACCATG|GCCCACCTCA|TCAGCCCTCT|GCCCTCCCCC|240|
|ACGGGAACCA|TCAGCGCTGC|AAACTCCTGC|CCCTCCAGCC|CCGGGGAGC|GGGGTCTTCA|300|
|GGGTACAAGG|TGGGCCGAGT|GATGCCATCT|GACCTCAATT|TAATGGCTGA|CAACTCACAG|360|

| | | | | | |
|---|---|---|---|---|---|
| CCTGAAAATG | AAAAGGAAGC | TTCAGGTGGA | GACAGCCCGA | AGGATGATTC | AAAGCCGCCT 420 |
| TACTCCTACG | CGCAGCTGAT | AGTTCAGGCG | ATTACGATGG | CTCCCGACAA | ACAGCTCACC 480 |
| CTGAACGGGA | TTTATACACA | CATCACTAAA | AATTATCCCT | ACTACAGGAC | TGCGGACAAG 540 |
| GGCTGGCACA | ATTCAATTCG | CCACAATCTC | TCTCTGAATC | GTTATTTCAT | CAAAGTGCCG 600 |
| CGTTCCCAGG | AAGAACCAGG | CAAAGGCTCG | TTCTGGAGGA | TAGACCCAGC | CTCTGAAAGC 660 |
| AAATTAATAG | AACAGGCTTT | TAGGAAACGA | CGGCCTAGGG | GCGTGCCCTG | CTTTAGAACC 720 |
| CCTCTGGGAC | CGCTCTCTTC | TAGGAGTGCC | CCAGCCTCTC | CCAATCACGC | GGGAGTGCTG 780 |
| TCTGCTCACT | CTAGTGGCGC | CCAGACCCCT | GAGAGCCTGT | CGAGGGAAGG | TTCGCCGGCC 840 |
| CCCCTGGAGC | CTGAGCCTGG | CGCTGCACAG | CCCAAACTCG | CTGTCATCCA | GGAAGCCCGG 900 |
| TTTGCCCAGA | GCGCCCAGG | GTCACCTCTG | TCCAGTCAGC | CAGTCTTAAT | CACCGTCCAG 960 |
| CGGCAGCTAC | CACAGGCCAT | CAAGCCTGTC | ACCTACACTG | TGGCCACCCC | AGTGACCACC 1020 |
| TCGACCTCCC | AGCCACCCGT | CGTGCAGACG | GTTCACGTCG | TCCACCAGAT | CCCAGCGGTG 1080 |
| TCGGTCACCA | GTGTGGCCGG | ACTGGCCCCA | GCGAACACGT | ACACTGTCTC | TGGACAAGCT 1140 |
| GTGGTCACCC | CGGCAGCCGT | GCTGGCCCCT | CCTAAGGCAG | AGGCCCAGGA | GAATGGAGAC 1200 |
| CACAGGGAAG | TCAAAGTGAA | AGTAGAGCCT | ATTCCCGCCA | TTGGCCACGC | CACGCTCGGC 1260 |
| ACTGCCAGCC | GGATCATTCA | GACGGCACAG | ACCACCCCGG | TCCAGACGGT | GACCATAGTA 1320 |
| CAACAGGCAC | CTCTAGGTCA | ACACCAGCTA | CCAATAAAAA | CTGTAACACA | AAACGGCACT 1380 |
| CACGTGGCAT | CAGTCCCCAC | TGCGGTCCAC | GGCCAGGTGA | ACAATGGGCC | CCTTGGCCTC 1440 |
| AGAAGGCCCC | CATGTGCCAG | CTCAGACTGG | AGTTGCCTCA | GTTGACACAG | CAGGCCCCAT 1500 |
| CCAGACAGAC | CAGCAGGTGC | TTCTGGAGAC | AAGAGCAAAG | CCTTTTCCGG | CAGCCGGGAA 1560 |
| CCTGGGATGA | GAAACGACAG | GTGGAAGGTT | GTCCAGAGAC | ACCTACAGCG | TGGATGCTGT 1620 |
| TCCGAGTCAG | CGTAGGAGAA | AGGCCACTGG | AAACCAGAGT | CACACTGCGC | GTCTGTGCAT 1680 |
| CTCTGGCCTA | CCGCAGTGGC | CCCGGCTGTC | TGCACATTTT | TTGTAGACAC | ATTAGAGTCG 1740 |
| GTTGAGGCCA | CACCTGCGGC | CACACCTGCG | GCCACAGACT | GCGACCGCGA | TTGCAGGGAG 1800 |
| GAGCATCTGA | GGTGGTCACG | GGGTGTGCCC | AGCTCACACC | AACTGCAGCC | GCGGCGAGTC 1860 |
| CTTTGCACAT | GTTGGCAACA | CACGCATCCG | CATCGGCCTC | CCTGCCCACA | AAGCGCCACA 1920 |
| ACGGTGACCA | GCCGGAGCAG | CCGGAGCTGA | AGCGGATCAA | GACAGAAGAC | GGCGAGGGCA 1980 |
| TCGTCATTGC | CCTGAGCGTG | GACACGCCAC | CGGCAGCCGT | AAGGGAAAAG | GGTGTCCAGA 2040 |
| ACTAGCGACC | GGGAGAGCTT | TTCTTAACG | ATATCAACTC | TGTGGTGCCA | AAAGGAGACG 2100 |
| CGGCCTCCCG | CCAGCACTCG | GGGGTGCAGG | GCCCTGTGGT | TGGACTTCAC | CTCTCAGCAC 2160 |
| TGAAAACCCA | AAACCCAGCT | GGCCTTAACA | CTCCTTAAAG | ACAGAAGTCA | CACTTGAACA 2220 |
| AAACCCACAC | ACAACAAAAC | CTGATTTGGG | AGACGGTGTC | TCCACTGAGC | ACCTGCTGGG 2280 |
| CTGAGCTTCT | ACCTACGAGT | GAAACTCTGT | CCTCCCGCGA | GGACCAGGCA | TCGCTGTGTG 2340 |
| AGGACGGCAC | GGCCAGCGCC | TGCTGTGAGT | GGGTCTCCCA | AGACTAGGCC | TCAGGACGCG 2400 |
| GGGGGAGCCA | TCCCCGCCGC | CCTCACAGGA | CCCACCAGGC | AGCGGAGACA | TGTGGAATTA 2460 |
| GAGTATTTTG | AGGTGTCCTT | TCTTTACAAA | ATAATGGGGT | CTTGGGCATT | TCACATCACT 2520 |
| CCATTTCTAC | TGAGACTTTC | AGAATCACAC | AGGCCCTTTC | CGTGGATTTC | ATTTGGGGCA 2580 |
| AAGAAACAAC | ATAGTTTTGT | TTTGTTTTC | AGCCTATGGA | ATGATTTCCT | TTTGTCTGTC 2640 |
| TTGTTCAAGT | TCAGACGAAG | CTACTCTGGC | ATCTGCACAT | TCCGTGTTA | CAGCAGCTGC 2700 |
| CTGATGAATT | TTATCCACCT | CCATTTCAGC | ATGTGGCTCG | CGTGGACAGG | TGGACGGACG 2760 |

```
CTGTGGCCGC ATGGAACCTT GAGAACCCAG GGACGAGCCA GTGCCGGGAA GGAACTGCCG   2820

GGACTCACCG AGCTGCACTT AACTGTTCTC TTTCTGGCTA TTTTTTGTTG TTTGTTTCTT   2880

TGTGTTGACT TTGTCCCTGG CAAAATTTTC CACTCTGAGT AAAACAAGTC TCGGAATTC    2939
```

(2) INFORMATION FOR SEQ ID NO:4:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Asp Ser Lys Pro Pro Tyr Ser Tyr Ala Gln Leu Ile Val Gln Ala Ile
 1               5                  10                  15

Thr Met Ala Pro Asp Lys Gln Leu Thr Leu Asn Gly Ile Tyr Thr His
                20                  25                  30

Ile Thr Lys Asn Tyr Pro Tyr Tyr Arg Thr Ala Asp Lys Gly Trp Gln
                35                  40                  45

Asn Ser Ile Arg His Asn Leu Ser Leu Asn Arg Tyr Phe Ile Lys Val
        50                  55                  60

Pro Arg Ser Gln Glu Glu Pro Gly Lys Gly Ser Phe Trp Arg Ile Asp
65                  70                  75                  80

Pro Ala Ser Glu Ser Lys Leu Ile Glu Gln Ala Phe Arg Lys Arg Arg
                85                  90                  95

Pro Arg
```

(2) INFORMATION FOR SEQ ID NO:5:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
His Ala Lys Pro Pro Tyr Ser Tyr Ile Ser Leu Ile Thr Met Ala Ile
 1               5                  10                  15

Gln Asn Asn Pro Thr Arg Met Leu Thr Leu Ser Glu Ile Tyr Gln Phe
                20                  25                  30

Ile Met Asp Leu Phe Pro Phe Tyr Arg Gln Asn Gln Gln Arg Trp Gln
                35                  40                  45

Asn Ser Ile Arg His Ser Leu Ser Phe Asn Asp Cys Phe Val Lys Ile
        50                  55                  60

Pro Arg Thr Pro Asp Lys Pro Gly Lys Gly Ser Phe Trp Thr Leu His
65                  70                  75                  80

Pro Asp Ser Gly Asn Met Phe Glu Asn Gly Cys Tyr Leu Arg Arg Gln
                85                  90                  95

Lys Arg
```

(2) INFORMATION FOR SEQ ID NO:6:

(i) SEQUENCE CHARACTERISTICS:
        (A) LENGTH: 98 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:6:

```
His Ala Lys Pro Pro Tyr Ser Tyr Ile Ser Leu Ile Thr Met Ala Ile
1               5                   10                  15

Gln Gln Ala Pro Ser Lys Met Leu Thr Leu Ser Glu Ile Tyr Gln Trp
            20                  25                  30

Ile Met Asp Leu Phe Pro Tyr Tyr Arg Gln Asn Gln Gln Arg Trp Gln
        35                  40                  45

Asn Ser Ile Arg His Ser Leu Ser Phe Asn Ala Cys Phe Val Lys Val
    50                  55                  60

Ala Arg Ser Pro Asp Lys Pro Gly Lys Gly Ser Tyr Trp Thr Leu His
65              70                  75                      80

Pro Asp Ser Gly Asn Met Phe Glu Asn Gly Cys Tyr Leu Arg Arg Gln
                85                  90                  95

Lys Arg
```

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:7:

AGAAAGGAGG AAAAA                    15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:8:

CCAATGAAGG AGAGA                    15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:9:

GACGCGGAGA AAGAA                    15

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:10:

CCAAGTGAGG AACCA 15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:11:

CTGAAAGAGG AACTT 15

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: linear ( x i ) SEQUENCE DESCRIPTION: SEQ ID NO:12:

Gly Ala Gly Ser Ser Gly
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

Arg Lys Arg Arg Pro Arg
1               5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

Arg Thr Pro Leu Gly Pro Leu Ser Ser
1               5

( 2 ) INFORMATION FOR SEQ ID NO:15:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:15:

GAAGAGGCCA ATGAAGGAGA GAACAACA                28

( 2 ) INFORMATION FOR SEQ ID NO:16:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:16:

GAGGACGCGG AGAAAGAAGT GTTAGTGTG              29

( 2 ) INFORMATION FOR SEQ ID NO:17:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:17:

GTCGTGGCCT CTGTCTAGTG TGGCAACA               28

( 2 ) INFORMATION FOR SEQ ID NO:18:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:18:

AATTGGAGGA AAA                                13

( 2 ) INFORMATION FOR SEQ ID NO:19:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:19:

ACTGTTTCAT ACAGAAGGCG T                                                                                          21

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:20:

GGTTCCTCCT TGGCTGACGT                                                                                            20

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:21:

CAGAGAGAGA                                                                                                       10

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:22:

GAAGTTCAGA TGACTAACTC A                                                                                          21

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO:23:

AATTGGAGGA AAAACTGTTT CATACAGAAG GCGT                                                                            34

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

( v ) FRAGMENT TYPE: linear ( x i ) SEQUENCE DESCRIPTION: SEQ ID NO:24:

GAAGAGGCCA ATGAAGGAGA GAACAACA                                                          28

( 2 ) INFORMATION FOR SEQ ID NO:25:

( i ) SEQUENCE CHARACTERISTICS:
                  ( A ) LENGTH: 30 base pairs
                  ( B ) TYPE: nucleic acid
                  ( C ) STRANDEDNESS: single
                  ( D ) TOPOLOGY: linear ( i i ) MOLECULE TYPE: other nucleic acid
                  ( A ) DESCRIPTION: /desc ="DNA"

( x i ) SEQUENCE DESCRIPTION: SEQ ID NO:25:

GAGGACGCGG AGAAAGAAGT GTTAAGTGTG                                                         30

( 2 ) INFORMATION FOR SEQ ID NO:26:

( i ) SEQUENCE CHARACTERISTICS:
                  ( A ) LENGTH: 31 base pairs
                  ( B ) TYPE: nucleic acid
                  ( C ) STRANDEDNESS: single
                  ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:26:

TGGAGTTGAC TAAGTCAATA ATCAGAATGA G                                                       31

( 2 ) INFORMATION FOR SEQ ID NO:27:

( i ) SEQUENCE CHARACTERISTICS:
                  ( A ) LENGTH: 21 base pairs
                  ( B ) TYPE: nucleic acid
                  ( C ) STRANDEDNESS: single
                  ( D ) TOPOLOGY: linear ( i i ) MOLECULE TYPE: DNA (genomic)

( v ) FRAGMENT TYPE: linear ( x i ) SEQUENCE DESCRIPTION: SEQ ID NO:27:

GAAGTTCAGA TGACTAACTC A                                                                  21

( 2 ) INFORMATION FOR SEQ ID NO:28:

( i ) SEQUENCE CHARACTERISTICS:
                  ( A ) LENGTH: 20 base pairs
                  ( B ) TYPE: nucleic acid
                  ( C ) STRANDEDNESS: single
                  ( D ) TOPOLOGY: linear ( i i ) MOLECULE TYPE: other nucleic acid
                  ( A ) DESCRIPTION: /desc ="dna"

( x i ) SEQUENCE DESCRIPTION: SEQ ID NO:28:

AGCTGATAGT TCAGGCGATT                                                                    20

( 2 ) INFORMATION FOR SEQ ID NO:29:

( i ) SEQUENCE CHARACTERISTICS:
                  ( A ) LENGTH: 20 base pairs
                  ( B ) TYPE: nucleic acid
                  ( C ) STRANDEDNESS: single (D) TOPOLOGY: linear (ii) MOLECULE TYPE: other nucleic acid
    (A) DESCRIPTION: /desc ="DNA"

(xi) SEQUENCE DESCRIPTION: SEQ ID NO:29:

ACAGAGTTGA TATCGTTAAA                                                                 20

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="DNA"

(xi) SEQUENCE DESCRIPTION: SEQ ID NO:30:

AGGAGAATGG AGACCACAGG GAAGT                                                           25

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="DNA"

(xi) SEQUENCE DESCRIPTION: SEQ ID NO:31:

CTGCTGTGTC AACTGAGGCA                                                                 20

(2) INFORMATION FOR SEQ ID NO:32:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="DNA"

(xi) SEQUENCE DESCRIPTION: SEQ ID NO:32:

AACAATGCCG CGGC                                                                       14

(2) INFORMATION FOR SEQ ID NO:33:

(i) SEQUENCE CHARACTERISTICS:
        (A) LENGTH: 494 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Val  Phe  Val  Asp  Gly  Val  Phe  Gln  Arg  Arg  Gly  Ala  Pro  Pro  Leu  Gln
 1              5                        10                           15

Leu  Pro  Arg  Val  Cys  Thr  Phe  Arg  Phe  Pro  Ser  Thr  Asn  Ile  Lys  Ile
               20                        25                           30

Thr  Phe  Thr  Ala  Leu  Ser  Ser  Glu  Lys  Arg  Glu  Lys  Gln  Glu  Ala  Ser
          35                        40                           45

Glu  Ser  Pro  Val  Lys  Ala  Val  Gln  Pro  His  Ile  Ser  Pro  Leu  Thr  Ile
```

```
            50                      55                      60
Asn  Ile  Pro  Asp  Thr  Met  Ala  His  Leu  Ile  Ser  Pro  Leu  Pro  Ser  Pro
65                       70                       75                       80

Thr  Gly  Thr  Ile  Ser  Ala  Ala  Asn  Ser  Cys  Pro  Ser  Ser  Pro  Arg  Gly
                    85                       90                       95

Ala  Gly  Ser  Ser  Gly  Tyr  Lys  Val  Gly  Arg  Val  Met  Pro  Ser  Asp  Leu
               100                      105                      110

Asn  Leu  Met  Ala  Asp  Asn  Ser  Gln  Pro  Glu  Asn  Glu  Lys  Glu  Ala  Ser
          115                      120                      125

Gly  Gly  Asp  Ser  Pro  Lys  Asp  Asp  Ser  Lys  Pro  Pro  Tyr  Ser  Tyr  Ala
     130                      135                      140

Gln  Leu  Ile  Val  Gln  Ala  Ile  Thr  Met  Ala  Pro  Asp  Lys  Gln  Leu  Thr
145                      150                      155                      160

Leu  Asn  Gly  Ile  Tyr  Thr  His  Ile  Thr  Lys  Asn  Tyr  Pro  Tyr  Tyr  Arg
                    165                      170                      175

Thr  Ala  Asp  Lys  Gly  Trp  His  Asn  Ser  Ile  Arg  His  Asn  Leu  Ser  Leu
               180                      185                      190

Asn  Arg  Tyr  Phe  Ile  Lys  Val  Pro  Arg  Ser  Gln  Glu  Glu  Pro  Gly  Lys
          195                      200                      205

Gly  Ser  Phe  Trp  Arg  Ile  Asp  Pro  Ala  Ser  Glu  Ser  Lys  Leu  Ile  Glu
     210                      215                      220

Gln  Ala  Phe  Arg  Lys  Arg  Arg  Pro  Arg  Gly  Val  Pro  Cys  Phe  Arg  Thr
225                      230                      235                      240

Pro  Leu  Gly  Pro  Leu  Ser  Ser  Arg  Ser  Ala  Pro  Ala  Ser  Pro  Asn  His
                    245                      250                      255

Ala  Gly  Val  Leu  Ser  Ala  His  Ser  Ser  Gly  Ala  Gln  Thr  Pro  Glu  Ser
               260                      265                      270

Leu  Ser  Arg  Glu  Gly  Ser  Pro  Ala  Pro  Leu  Glu  Pro  Glu  Pro  Gly  Ala
          275                      280                      285

Ala  Gln  Pro  Lys  Leu  Ala  Val  Ile  Gln  Glu  Ala  Arg  Phe  Ala  Gln  Ser
     290                      295                      300

Ala  Pro  Gly  Ser  Pro  Leu  Ser  Ser  Gln  Pro  Val  Leu  Ile  Thr  Val  Gln
305                      310                      315                      320

Arg  Gln  Leu  Pro  Gln  Ala  Ile  Lys  Pro  Val  Thr  Tyr  Thr  Val  Ala  Thr
                    325                      330                      335

Pro  Val  Thr  Thr  Ser  Thr  Ser  Gln  Pro  Pro  Val  Val  Gln  Thr  Val  His
               340                      345                      350

Val  Val  His  Gln  Ile  Pro  Ala  Val  Ser  Val  Thr  Ser  Val  Ala  Gly  Leu
          355                      360                      365

Ala  Pro  Ala  Asn  Thr  Tyr  Thr  Val  Ser  Gly  Gln  Ala  Val  Val  Thr  Pro
     370                      375                      380

Ala  Ala  Val  Leu  Ala  Pro  Pro  Lys  Ala  Glu  Ala  Gln  Glu  Asn  Gly  Asp
385                      390                      395                      400

His  Arg  Glu  Val  Lys  Val  Lys  Val  Glu  Pro  Ile  Pro  Ala  Ile  Gly  His
                    405                      410                      415

Ala  Thr  Leu  Gly  Thr  Ala  Ser  Arg  Ile  Ile  Gln  Thr  Ala  Gln  Thr  Thr
               420                      425                      430

Pro  Val  Gln  Thr  Val  Thr  Ile  Val  Gln  Gln  Ala  Pro  Leu  Gly  Gln  His
          435                      440                      445

Gln  Leu  Pro  Ile  Lys  Thr  Val  Thr  Gln  Asn  Gly  Thr  His  Val  Ala  Ser
     450                      455                      460

Val  Pro  Thr  Ala  Val  His  Gly  Gln  Val  Asn  Asn  Gly  Pro  Leu  Gly  Leu
465                      470                      475                      480
```

```
Arg  Arg  Pro  Pro  Cys  Ala  Ser  Ser  Asp  Trp  Ser  Cys  Leu  Ser
               485                         490
```